(12) United States Patent
Sinko et al.

(10) Patent No.: US 9,999,596 B2
(45) Date of Patent: Jun. 19, 2018

(54) CONTROLLED RELEASE HYDROGELS

(71) Applicant: Rutgers, The State University of New Jersey, New Brunswick, NJ (US)

(72) Inventors: Patrick J. Sinko, Lebanon, NJ (US); Stanley Stein, East Brunswick, NJ (US); Anita Lalloo, Berwyn, PA (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days. days.

(21) Appl. No.: 14/656,361

(22) Filed: Mar. 12, 2015

(65) Prior Publication Data

US 2015/0283077 A1 Oct. 8, 2015

Related U.S. Application Data

(62) Division of application No. 14/453,968, filed on Aug. 7, 2014, now abandoned, which is a division of application No. 11/793,566, filed as application No. PCT/US2005/046891 on Dec. 22, 2005, now abandoned.

(60) Provisional application No. 60/638,552, filed on Dec. 22, 2004.

(51) Int. Cl.
| | |
|---|---|
| *A61K 9/127* | (2006.01) |
| *A61K 9/00* | (2006.01) |
| *A61K 31/4745* | (2006.01) |
| *A61K 47/34* | (2017.01) |

(52) U.S. Cl.
CPC ............ *A61K 9/127* (2013.01); *A61K 9/0019* (2013.01); *A61K 9/0024* (2013.01); *A61K 31/4745* (2013.01); *A61K 47/34* (2013.01)

(58) Field of Classification Search
CPC ..................................................... A61K 9/127
See application file for complete search history.

(56) References Cited

U.S. PATENT DOCUMENTS

| | | | | |
|---|---|---|---|---|
| 4,681,582 A | * | 7/1987 | Yamamoto .......... | A61M 31/002 424/450 |
| 5,631,018 A | | 5/1997 | Zalipsky et al. | |
| 5,853,755 A | * | 12/1998 | Foldvari .............. | A61K 9/0014 264/4.1 |
| 6,051,648 A | * | 4/2000 | Rhee ..................... | A61L 24/043 525/419 |
| 6,284,375 B1 | * | 9/2001 | Jin ........................ | A61K 9/127 424/1.21 |
| 6,312,720 B1 | | 11/2001 | Katinger et al. | |

(Continued)

FOREIGN PATENT DOCUMENTS

| | | |
|---|---|---|
| EP | 0088642 | 9/1983 |
| EP | 0056962 | 10/1985 |

(Continued)

OTHER PUBLICATIONS

U.S. Appl. No. 14/453,968, filed Aug. 7, 2014, Controlled Release Hydrogels.

(Continued)

*Primary Examiner* — Gollamudi Kishore
(74) *Attorney, Agent, or Firm* — Fox Rothschild LLP

(57) ABSTRACT

Formulations and methods for their preparation including a hydrogel including a crosslinked matrix comprising a polymer, and a one or more liposomes containing a therapeutic agent.

15 Claims, 10 Drawing Sheets

(56) References Cited

U.S. PATENT DOCUMENTS

| | | | |
|---|---|---|---|
| 6,475,516 B2 * | 11/2002 | DiCosmo | A61L 27/34 424/443 |
| 6,740,335 B1 * | 5/2004 | Moynihan | A61K 9/127 264/4.1 |
| 7,104,894 B2 | 9/2006 | Bennett | |
| 9,211,358 B2 | 12/2015 | Sinko et al. | |
| 2002/0122785 A1 | 9/2002 | Stein et al. | |
| 2003/0133973 A1 * | 7/2003 | Slater | A61K 9/1271 424/450 |
| 2004/0067976 A1 * | 4/2004 | Priestley | C07D 235/18 514/303 |
| 2006/0134226 A1 | 6/2006 | Leonard | |

FOREIGN PATENT DOCUMENTS

| | | |
|---|---|---|
| EP | 0325247 | 5/1993 |
| EP | 0296612 | 6/1994 |
| EP | 0540099 | 4/1996 |
| EP | 0321122 | 9/1996 |
| EP | 0737686 | 7/1999 |
| WO | 1990/003169 | 4/1990 |
| WO | 1996/037496 | 11/1996 |
| WO | 1996/038146 | 12/1996 |
| WO | 1996/038449 | 12/1996 |
| WO | 1997/000876 | 1/1997 |

OTHER PUBLICATIONS

U.S. Appl. No. 11/793,566, filed Jan. 24, 2008, Controlled Release Hydrogels.

Information about Related Patents and Patent Applications, see section 6 of the accompanying Information Disclosure Statement Letter, which concerns Related Patents and Patent Applications.

International Search Report issued in Application No. PCT/US2005/046891 dated Jun. 19, 2006.

International Preliminary Report on Patentability issued in Application No. PCT/US2005/046891 dated Jun. 26, 2007.

Emerson et al., "In Vivo Antitumor Activity of Two New Seven-substituted Water-Soluble Camptothecin Analogues," Canc Res, 1995, vol. 55, No. 3, pp. 603-609 (Abstract only).

Gregoriadis, "Immunological adjuvants: A role for liposomes," Immunol Today, 1990, vol. 11, pp. 89-97 (Abstract only).

* cited by examiner

CONTROLLED RELEASE HYDROGELS

This application is a divisional of U.S. patent application Ser. No. 14/453,968, filed Aug. 7, 2014, which is a divisional of U.S. patent application Ser. No. 11/793,566, filed Jan. 24, 2008, which is the U.S. National Stage of International patent application no. PCT/US2005/046891, filed Dec. 22, 2005, which claims priority from U.S. provisional application No. 60/638,552, filed Dec. 22, 2004, the disclosures of which are hereby incorporated by reference in their entireties.

FIELD OF THE INVENTION

The present invention relates to formulations and methods for their preparation, that comprise a hydrogel including a cross-linked matrix comprising a polymer, and a one or more liposomes containing a therapeutic agent. Such formulations provide for the controlled release of the therapeutic agent for uses including the prophylaxis or treatment of conditions and diseases.

BACKGROUND OF THE INVENTION

Hydrogels are three dimensional, hydrophilic, polymeric networks which swell in water without dissolving and retain large quantities of water. They typically comprise both natural polymers such as starches and cellulose derivatives and synthetic polymers and copolymers such as polyethylene glycol and poly(glutamic acid). The networks within the hydrogel can be crosslinked either chemically or physically by cohesive bonds such as ionic interaction, hydrogen bonding or hydrophobic interactions. Alginates and chitosans are examples of polymers that are cross-linked by ionic interactions. Hydrogels are suitable for numerous applications such as implants, contact lenses, membranes for isosensors and drug delivery devices. Drugs may be incorporated in the hydrogel matrix by either mixing the copolymer together with the drug prior to the addition of the crosslinker which initiates polymerization or by placing the preformed hydrogel in the drug solution until it swells to equilibrium.

Hydrogels can be used to release drugs slowly over time, to protect drugs from degradation or to trigger drug release in response to various stimuli such as, for example, temperature, insulin blood levels or inflammation. Due to their high water content and soft and elastic consistency, hydrogels resemble natural tissue causing minimal mechanical irritation.

However, hydrogels typically are found to be unsuitable as controlled drug delivery devices for low molecular weight hydrophilic compounds because the high water content of the hydrogel and the presence of large pores results in rapid drug release.

There exits a need in the art for hydrogel compositions which are useful for the controlled release administration of low molecular weight therapeutically active agents and other therapeutically active agents which have been found to be difficult to administer over a prolonged period of time with hydrogels.

SUMMARY OF THE INVENTION

It is an object of the present invention to provide a sustained release pharmaceutical composition suitable for the administration of a therapeutically active agent over a prolonged period of time.

It is a further object of certain embodiments of the present invention to provide a sustained release hydrogel composition suitable for the administration of a low molecular weight therapeutically active agent over a prolonged period of time.

It is a further object of certain embodiments of the present invention to provide a pharmaceutical composition suitable for site-specific therapy with a therapeutically active agent over a prolonged period of time.

It is a further object of certain embodiments of the present invention to provide a sustained release hydrogel composition including at least one cross-linked polymer and a plurality of liposomes containing a therapeutically active agent, wherein the hydrogel composition is suitable for the administration of the therapeutically active agent over a prolonged period of time.

It is a further object of certain embodiments of the present invention to provide a sustained release hydrogel composition suitable for the administration of camptothecin, a pharmaceutically acceptable salt or derivative thereof over a prolonged period of time to a mammal in need of camptothecin therapy.

It is a further object of certain embodiments of the present invention to provide a controlled release formulation capable of continuously delivering the active lactone form of camptothecin, pharmaceutically acceptable salts thereof or derivatives thereof over a prolonged period of time.

It is a further object of certain embodiments of the present invention to provide a method of treatment of certain forms of cancer via site-specific administration of a hydrogel composition including an anti-tumor agent to a mammal in need of such treatment.

It is a further object of certain embodiments of the present invention to provide a pharmaceutical hydrogel composition including a therapeutic agent and methods of administration which provides for prolonged release of the therapeutic agent in the affected region, with low systemic concentrations and few concurrent side effects.

It is a further object of certain embodiments of the present invention to provide a pharmaceutical composition providing for enhanced bioavailability of anti-tumor therapeutic agents.

It is a further object of certain embodiments of the present invention to provide an absorbable pharmaceutical composition that enhances the targetability of liposomal encapsulated pharmaceutically active agent, and which may be readily prepared and administered.

The above-mentioned objects and others are achieved by virtue of the present invention, which is directed in part to a sustained release pharmaceutical composition comprising a hydrogel including a cross-linked polymer matrix and at least one liposome containing a therapeutically active agent wherein the at least one liposome is dispersed in the matrix, and the therapeutically active agent is released over a prolonged period of time upon administration to a mammal.

In certain embodiments, the invention is directed to a sustained release pharmaceutical composition comprising a hydrogel including at least one cross-linked polymer and an encapsulated therapeutically active agent, wherein the encapsulated therapeutically active agent is release over a prolonged period of time upon administration to a mammal.

In certain embodiments, the invention is further directed to a sustained release pharmaceutical composition comprising a hydrogel including cross-linked polymer matrix comprising at least one cross-linked polymer and a plurality of liposomes including a therapeutically active agent, wherein the liposomes are dispersed in the cross-linked polymer matrix and the therapeutically active agent is release over a prolonged period of time upon administration to a mammal.

In certain embodiments, the present invention is directed to an in situ forming hydrogel, in which liposomes including a therapeutically active agent are physically entrapped and delivery controlled amounts of the active agent over a prolonged period of time such that the plasma concentrations are within the therapeutic range for treatment with the therapeutically active agent.

In certain preferred embodiments, the pharmaceutical composition preferably releases the therapeutically active agent over a prolonged period of time, preferably over a period of several hours, days, weeks, or months duration. A particularly preferred embodiment releases the therapeutically active agent at the same release rate or substantially the same release rate over the prolonged period of time.

Preferably the therapeutic agent for use in accordance with the present invention is suitable for encapsulation in a liposome or a plurality of liposomes.

In certain preferred embodiments, the therapeutically active agent is a low-molecular weight therapeutically active agent. In certain preferred embodiments, the therapeutically active agent is camptothecin, a pharmaceutically acceptable salt, analog, or derivative thereof.

In certain embodiments, the invention is further directed to method of preparing a sustained release pharmaceutical composition suitable for the administration of a low molecular weight therapeutic agent over a prolonged period of time, by encapsulating the low molecular weight therapeutic agent in a liposome or a plurality of liposomes and incorporating the encapsulated therapeutic agent in hydrogel including a cross-linked polymeric matrix.

In certain embodiments, the present invention is further directed to a method for preparing a formulation in accordance with the present invention comprising preparing a mixture of at least two phases, one of which is at least one polymer capable of being cross-linked and forming cross-links between the polymer molecules. The second phase is dispersed in the polymeric phase and is in the form of liposomes which include the therapeutically active agent and which preferably surrounds and/or encapsulates the therapeutically active agent. In certain embodiments, the second phase (e.g., the liposomes) are physically entrapped within the polymer matrix of the invention. Such physical entrapment generally relates to and refers to the cross-linking of the polymer which preferably non-covalently entraps the liposomes.

In certain preferred embodiments, the present invention is further directed to a pharmaceutical composition comprising a hydrogel cross-linked with polyethylene glycol (PEG) or a derivative thereof; and dispersed within the hydrogel is a liposomal encapsulated anti-tumor agent such as camptothecin or pharmaceutically acceptable salt or derivative thereof, wherein the anti-tumor agent is release over a prolonged period of time upon administration to a mammal.

Preferably when the pharmaceutical compositions of the present invention include camptothecin or a pharmaceutically acceptable salt or derivative thereof, the pharmaceutical compositions inhibit the hyperproliferation of cells, including cancerous cells. Preferably the present invention is further directed to methods of inhibiting the hyperproliferation of cells, including cancerous cells.

In certain embodiments, the liposomal encapsulated drug particles to be incorporated in the hydrogel matrix can further include excipients and/or polymers described herein.

In certain embodiments, the pharmaceutically active agent can be released from the liposomes through diffusion or dissolution of the liposomes, the hydrogel or both.

In certain preferred embodiments, the hydrogel compositions of the invention comprise a polymer matrix prepared from polymers bearing moieties, such as thiol moieties, which are capable of being cross-linked by any of a number of processes, such as oxidation or by use of a bifunctional cross-linking agent, to physically entrap the liposomes including the therapeutic agent within the cross-linked polymer. The matrices preferably are prepared by cross-linking the polymer in the presence of the liposomes, such that entrapment occurs during cross-linking. In certain preferred embodiments, the invention is further directed to compositions and pharmaceutical compositions prepared by these methods, methods of preparing the compositions by cross-linking the polymer to entrap the agent therein, as well as to methods for administering the composition to a mammal, for instance, by injecting the composition of the invention into an animal during the process of cross-linking such that the mixture is liquid or semi-solid during injection, but soon after injection completes the cross-linking process and forms the matrix (depot) with the aforementioned release characteristics. Thus, the cross-linking of the polymer may be performed during the manufacture of the composition, which is subsequently administered to or implanted at the desired site; in another embodiment, a mixture of the liposomes including the therapeutic agent(s), the polymer and the cross-linking agent is administered to the desired site at the time of or just after initiation of the cross-linking reaction, such that the mixture can be readily deposited at the desired site, and the cross-linking subsequently occurs or is completed in the bodily compartment to form the matrix. Preferably, the liposomes including the therapeutically active agent or agents are physically entrapped within the cross-linked polymer.

The term therapeutically active agent can refer to any therapeutically active substance capable of being administered in a particulate formulation, which achieves the desired effect. Pharmaceutically active agents can be synthetic or natural organic compounds, proteins or peptides, oligonucleotides or nucleotides, or polysaccharides or sugars. Drugs may have any of a variety of activities, which may be inhibitory or stimulatory, such as antibiotic activity, antiviral activity, antifungal activity, steroidal activity, cytotoxic or anti-proliferative activity, anti-inflammatory activity, analgesic or anesthetic activity, or be useful as contrast or other diagnostic agents. Preferably, the therapeutically active agent is a low molecular weight therapeutic agent such as camptothecin, or a pharmaceutically acceptable salt, analog or derivative thereof.

Liposomes for use in accordance with the present invention may or may not be spherical in shape. Liposomes are generally solid polymeric spheres, which can include a honeycombed structure formed by pores through the polymer which are filled with the active agent.

DETAILED DESCRIPTION

Figure 1A:
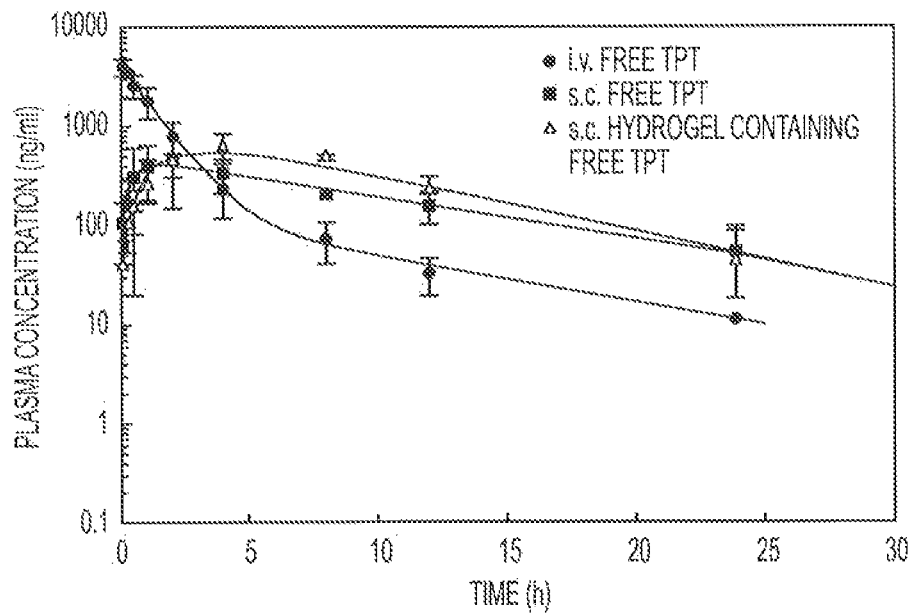
FIGS. 1A and B: Graphically depicts a comparison of the plasma concentration time-profiles of topotecan (TPT) after the administration of various dosage forms of TPT (10 mg/kg) to Fischer 344 Rats. Results represent the mean±SD of three animals.

Depending on the desired repository site of the hydrogel matrix composition of the invention, simply administering a therapeutic agent in the form of liposomes could have undesirable attributes. These liposomes may migrate from the injection site or may be subject to attack by macrophages or soluble degradative enzymes or antibodies, in contrast with the protective environment afforded by a gel. In addition, liposomes not contained within a gel may not be easily retrievable in case of an adverse side reaction. Preferably, the use of the hydrogel and liposomes maintain the stability of the active agents during residence in the instant compositions permitting the long-term use, and infrequent need to replace, the compositions of the invention.

Preferably the therapeutically active agent of the present invention is present as a dispersion of the liposomes including a therapeutically active agent in a hydrogel matrix. In certain embodiments, the hydrogel matrix can be used to cause the liposomes to remain at a particular location over an extended period of time, particularly when the hydrogel is administered to a mammal. Preferably, the hydrogel allows for local delivery of the therapeutically active agent.

Suitable hydrogels for use in accordance with the present invention can be formed from synthetic polymers such as polyethylene glycol, polyethylene oxide, polyvinyl alcohol, polyvinyl pyrrolidone, polyacrylates, poly (ethylene terephthalate), poly(vinyl acetate), and copolymers and blends thereof, as well as natural polymers such as cellulose and alginate.

Preferably, the polymer comprises at least two thiol groups, and may be a homopolymer or a copolymer.

The hydrogels of the present invention include at least one cross-linkable polymer which is cross-linked to entrap the encapsulated therapeutic agent. Any cross-linkable polymer, which bears two or more functional or reactive groups capable of participating in a cross-linking reaction to form a matrix of the invention may be used. Such functional groups include but are not limited to amino, carboxyl, thiol and hydroxyl groups, or combinations thereof; reactive groups include vinylsulfone, maleimide, pyridyldithio, and other moieties capable of reacting with the aforementioned functional groups, among others. A preferred polymer is one on which at least two thiol groups are present and is cross-linked with a thiol-reactive bifunctional cross-linking reagent in the presence of the encapsulated therapeutic agent, thus forming a cross-linked polymer with the liposome encapsulated therapeutic agent physically entrapped therein. Selection of the appropriate polymer, the concentration in the matrix, the extent of functional groups capable of participating in cross-linking, the type of cross-linking agent, and the extent of cross-linking, and other factors may be governed by the amount of liposome encapsulated therapeutic agent present in the composition in order to achieve the desired controlled release properties of the composition, or retention of the liposomes within the composition.

Examples of suitable polymers for the preparation of the polymer on which at least two thiol groups are present include both homopolymers or copolymers. By way of non-limiting example, suitable polymers, which may be chemically modified to comprise thiol groups, include polyalkylene oxides such as poly(ethylene glycol) [also known as polyethylene glycol or PEG, polyethylene oxide or PEO], carboxymethylcellulose, dextran, polyvinyl alcohol, N-(2-hydroxypropyl)methacrylamide, polyvinyl pyrrolidone, poly-1,3-dioxolane, poly-1,3,6-trioxane, polypropylene oxide, a copolymer of ethylene/maleic anhydride, a polylactide/polyglycolide copolymer, a polyaminoacid, a copolymer of poly(ethylene glycol) and an amino acid, or a polypropylene oxide/ethylene oxide copolymer. Such polymers are then derivatized or further polymerized to introduce thiol groups; chemical modification of the polymer may be necessary as a step prior to the further derivatization to incorporate thiol groups. In certain embodiments, for example, a polymer of the present invention may be derived from a poly(ethylene glycol) (PEG) derivative, for example, α,ω-dihydroxy-PEG or α,ω-diamino-PEG, but other derivatives are embraced herein. In certain embodiments the polymer comprising thiol groups may be, for example, a polymer of α,ω-diamino-poly(ethylene glycol) and thiomalic acid; a polymer of α,ω-dihydroxy-poly(ethylene glycol) and thiomalic acid; or a polymer of α,ω-dicarboxy-PEG subunits and lysine wherein the free carboxy groups on the lysine residues are derivatized to form thiol groups. These polymers are only examples of possible choices, as the skilled artisan will be aware of numerous alternatives. The selection of the polymer, or combinations thereof, may be guided by the desired properties of the final product such as, for example, the duration of release of the therapeutic agent and the release kinetics. In certain embodiments, a product of the invention may comprise more than one polymer component in order to provide two or more different release characteristics. In certain embodiments, more than one therapeutic agent may be included.

In certain preferred embodiments, a polymer of the present invention is derived from a poly(ethylene glycol) (PEG) derivative, for example, α,ω-dihydroxy-PEG or α,ω-diamino-PEG, but other derivatives are embraced herein. Examples of such polymers with particular molecular weights include α,ω-dihydroxy-PEG$_3$,-400; α,ω-dihydroxy-PEG$_{1,000}$; α,ω-diamino-PEG.$_{-3,400}$; and α,ω-diamino-PEG$_{1,000}$. PEG is known to be a particularly nontoxic polymer. These derivatized PEG subunit polymers may be used as amino- and hydroxy-containing polymers for cross-linking, or may be further derivatized, for example, to prepare the polymer on which at least two thiol groups are present by derivatization with thiomalic acid. Thiomalic acid (also known as mercaptosuccinic acid) may be replaced by dimercaptosuccinic acid, thereby doubling the number of sites available for cross-linking. Increasing the extent of cross-linking the matrix results in a gel with smaller pores.

In certain embodiments, the formulations of the invention are prepared from a mixture of polymer matrix and liposomes which comprises at least one therapeutic agent, preferably the polymer matrix including a polymer capable of being cross-linked, and forming cross-links between the polymer molecules to form a cross-linked matrix entrapping the liposomes included the therapeutic agent. In certain embodiments, the cross-linking can be performed before, during, or after the matrix is administered to a mammal. For example, the cross-linking reaction can be initiated in vitro, and the mixture, while undergoing cross-linking, may be injected into a bodily compartment of a mammal, wherein the injected bolus continues to cross-link and harden in situ. In certain embodiments, a cross-linked matrix after formation can be implanted or inserted into the location of the body from which delivery of the agent is desired. The compositions may also be introduced at either end of the gastrointestinal tract for transmucosal absorption.

In certain embodiments, the polymer moieties may be cross-linked by reagents capable of forming covalent bonds between the functional groups, such as but not limited to homobifunctional and heterobifunctional cross-linking agents. As described above, a preferred moiety is a thiol group. In certain embodiments, a preferred cross-linking agent is one that forms thioether bonds, such as a vinylsulfone or maleimide, but the invention is not so limiting. Other cross-linking reagents, such as a pyridyldithio-containing reagent, or oxidation, may be used to generate reducible cross-links. Combinations of cross-linking reagents may be used, to provide a ratio of cross-link types which generate the desired release characteristics of the composition. In certain embodiments, the preferred thiol-containing polymer has from 2 to about 20 thiol groups, preferably from about 3 to about 20 thiol groups, and most preferably from about 3 to about 8 thiol groups. In certain embodiments, the thiol groups on the polymer are sterically hindered.

Various conditions and/or reagents may be used to effect the cross-linking of the polymer, depending on the particular functional groups on the polymer. By way of non-limiting example, the conditions that cause cross-linking of the thiol groups on a thiol-containing polymer may be reaction in the presence of an oxidizing agent or reaction with a cross-linking agent. In the aspect of oxidation, the oxidizing agent may be by way of non-limiting example, molecular oxygen, hydrogen peroxide, dimethylsulfoxide, and molecular iodine. In the aspect where a cross-linking agent is used, the cross-linking agent may be a bifunctional disulfide-forming cross-linking agent or a bifunctional thioether-forming cross-linking agent. In a preferred embodiment, the cross-linking agent is a long-chain cross-linking agent, with a molecular weight of about 300 to about 5,000 Da. Non-limiting examples of suitable cross-linking agent include 1,4-di-[3',2'-pyridyldithio(propionamido)butane]; α,ω-di-O-pyridyldisulfidyl-poly(ethylene glycol); a vinyl sulfone such as α,ω-divinylsulfone-poly(ethylene glycol); 1,11-bis-maleimidotetraethylene glycol; and α,ω-diiodoacetamide-poly(ethylene glycol).

For other functional groups or a combination of a thiol group and another group, any appropriate bifunctional cross-linking agent may be selected which will achieve the desired cross-linking of the functional groups and formation of the cross-linked polymer.

In another aspect, the polymer additionally comprises a functional group, which may derivatized for example with a label, such as a contrast/imaging agent, radionuclide, chromophore, fluorophore, red or near-infrared fluorophore, or nonradioactive isotope. In certain embodiments, the label is a metabolically stable polymer component that after degradation of the polymer is detectable in the urine. In another embodiment, the cross-linking agent used to cross-link the polymer additionally comprises a functional group, such as a label.

In certain embodiments, the release rate of the therapeutic or other agent in the composition of the invention may be regulated by the biodegradability of the cross-linked polymer matrix, the liposome or combination thereof. In certain embodiments, the degradation rate may be adjusted by varying the ratio or types of cross-links of the matrix, and the stability or lability thereof, in the composition. For example, preferably, the ratio of reducing agent-sensitive disulfide bonds, esterase-sensitive ester bonds, and stable thioether bonds may be selected to provide the desired release kinetics of one or more entrapped liposomes. In certain embodiments, the release rate is adjusted by adjusting the pore size of the pores in the hydrogel matrix which allows for the release of the liposome from the matrix. For example, compounds or liposomes with molecular weights greater than the pore size of the hydrogel matrix will be trapped within the hydrogel and release slowly. In preferred embodiments, the concentration of the copolymer the type and amount of cross-linker and the solution pH can be manipulated to form hydrogels of varying pore size.

Liposomes for use in the present invention preferably are non-toxic, non-immunogenic, biocompatible, and biodegradable and may comprise various polymers.

The term "liposome" refers to a generally spherical or spheroidal cluster or aggregate of amphipathic compounds, including lipid compounds, typically in the form of one or more concentric layers, for example, bilayers. Liposomes typically represent a versatile drug carrier technology including an aqueous compartment entrapped by one or more bilayers of natural or synthetic lipids. Thus, drugs with various physicochemical properties can be encapsulated by either partitioning into the phospho lipids bilayer (hydrophobic drugs) or into the aqueous interior (water soluble drug) or the lipid-aqueous interface. The liposomes may be formulated e.g., from ionic lipids and/or non-ionic lipids. Liposomes may be unilamellar vesicles (possessing a single bilayer membrane) or multilamellar vesicles (onion-like structures characterized by multimembrane bilayers, each separated from the next by an aqueous layer. A general discussion of liposomes can be found in Gregoriadis G. (1990) Immunological adjuvants: A role for liposomes, Immunol. Today 11:89-97 the disclosure of which is hereby incorporated by reference.

The liposomes preferably comprise lipids which may be of either natural, synthetic or semi-synthetic origin, including for example, fatty acids, neutral fats, phosphatides, oils, glycolipids, surface-active agents (surfactants), aliphatic alcohols, waxes, terpenes and steroids.

Preferably, the liposomes comprise lipids such as, for example and without limitation, phospholipids such as naturally derived lecithin (e.g., egg yolk lecithin, soybean lecithin), phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids. Examples of phospholipids include, but are not limited to, phosphatidylcholines such as dipentadecanoylphosphatidylcholine dilauroylphosphatidylcholine, diarachidoylphosphatidylcholine (DAPC), dibehenoylphosphatidylcholine (DBPC), ditricosanoylphosphatidylcholine (DTPC), dilignoceroylphatidylcholine (DLPC), dipalmitoylphosphatidylcholine (DPPC), dimyristoylphosphatidylcho line (DMPC), distearoylphosphatidylcholine (DSPC), dioleoylphosphatidylcholine (DOPC), dimyristoylphosphatidylethanolamine (DMPE), diparmitoylphosphatidylglycerol (DPPG), and dimyristoylphosphatidic acid (DMPA); phosphatidylethanolamines such as dioleoylphosphatidylethanolamine or 1-hexadecyl-2-palmitoylglycerophosphoethanolamine, glycolipids such as glycosphingolipids and glyceroglycolipids; fatty acids; dialkylmethylammonium amphiphiles, polyglycerol alkylethers, polyoxyethylene alkylethers (Liposome Technology 2nd edition, Vol. 1, p. 141, 1993); alkyl glycosides; alkyl methylglucamides; alkyl sucrose esters; dialkyl polyoxyethylene ethers; dialkyl polyglycerol ethers (Liposome Technology 2nd edition, Vol. 1, p. 157, 1993); and amphipathic block copolymers such as polyoxyethylene/polylactic acids. These lipids may be used alone or in combination of two or more of them, and together with one or more non-polar substances such as cholesterol, if desired.

In certain embodiments the liposomes contain charged substances such as stearylamine and dicetyl phosphate; phospholipid derivatives having a water-soluble polymer-moiety such as polyethylene glycol; phospholipid derivatives having maleimide groups or the like.

Preferably, use of liposomes offer several advantages: such as they are non-toxic and biodegradable in composition; they display long circulation half-lives; and recognition molecules can be readily attached to their surface for targeting to tissues. Some examples of lipid-polymer conjugates and liposomes are disclosed in U.S. Pat. No. 5,631,018, which is incorporated herein by reference in its entirety.

Although any liposomes may be used in this invention, particularly useful liposomes use phospholipids and unesterified cholesterol in the liposome formulation. In certain embodiments, the cholesterol is used to stabilize the liposomes, however, any other compound that stabilizes liposomes may replace the cholesterol. Other liposome stabilizing compounds are known to those skilled in the art. Liposomes of different sizes and characteristics can be prepared using various techniques.

The physicochemical properties of the drug to some extent dictates the method selected. However, various processes can be included to improve encapsulation efficiency. The simplest method is the thin-film hydration procedure in which a thin film of lipids (in which the drug is dissolved if it's lipophilic) is hydrated with an aqueous phase above the transition temperature of the lipids. A heterogeneous distribution of multilamellar vesicles are produced using this method. These vesicles can be size reduced by sonication or extrusion to form a homogeneous liposome suspension.

In the reverse-phase evaporation technique water-in-oil emulsions of phospholipids and buffer in an excess of organic phase are subject to evaporation under reduced pressure to remove the organic phase resulting in the production of large unilamellar vesicles with a high aqueous space to lipid ratio. High drug entrapment efficiencies of 60-65% can be achieved. Hydrophilic drugs may be encapsulated by hydrating the lipid film with an aqueous solution of the drug. For hydrophilic drugs the encapsulation efficiency depends on the entrapped water volume which is governed by the particle size, number of bilayers and lipid concentration.

Amphiphilic drugs may be encapsulated into preformed liposomes with high efficiency using the "active loading" technique. Transmembrane pH gradients are utilized so that once the unionized drug enters the liposome by passive diffusion, it becomes charged due to the liposomal interior pH and thus is trapped and accumulates within the liposome. In certain embodiments, the pH gradient is destroyed with increased drug loading. This can be overcome by using ammonium sulfate gradients to generate a pH imbalance, which subsequently provides a driving force for the remote loading of amphipathic weak bases. Differences in calcium acetate concentrations across liposomal membranes have also been used to increase the loading of amphipathic weak acids. Ionophore-generated proton gradients using the ionophore A23187 have been described to improve the encapsulation efficiency of hydrophilic drugs. Numerous factors can be modified to produce liposomes with the desired properties. The type and the concentration of lipid typically controls the fluidity or rigidity, the stability and the drug release rate from the liposomes.

The liposome (e.g., liposome) for use in accordance with the present invention preferably encapsulates the therapeutically active agent and the resulting liposome-encapsulated therapeutic agent is then mixed with the polymer.

Delivery of small-molecule drugs, peptides, proteins, polysaccharides, and polynucleotides including antisense nucleotides are achievable using the compositions described herein. In certain preferably embodiments, small molecule therapeutic agents are preferred and may include, for example, anticancer drugs, cardiovascular drugs, antibiotics, antifungals, antiviral drugs, AIDS drugs such as HIV-1 protease inhibitors and reverse transcriptase inhibitors, antinociceptive (pain) drugs, hormones, vitamins, anti-inflammatory drugs, angiogenesis drugs, and anti-angiogenesis drugs. Particularly useful in according with the present invention are low molecular weight therapeutic agents.

Particularly preferred therapeutic agents are anti-cancer or anti-tumor agents. In particular, camptothecins, pharmaceutically acceptable salts or analogs thereof, such as, topotecan, irinotecan, homocaptothecins, homosilatecans, pharmaceutically acceptable salts thereof and the like (all are herein referred to as CPTs). Other camptothecin analogs or derivatives for use in accordance with the compositions of the present invention have also been described, for example, in the patents or patent applications EP 56,692, EP 88,642, EP 296,612, EP 321,122, EP 325,247, EP 540,099, EP 737,686, WO 90/03169, WO 96/37496, WO 96/38146, WO 96/38449, WO 97/00876, U.S. Pat. No. 7,104,894, JP 57 116,015, JP 57 116,074, JP 59 005,188, JP 60 019,790, JP 01 249,777, JP 01 246,287 and JP 91 012,070 or in Canc. Res., 38 (1997) Abst. 1526 or 95 (San Diego-12-16 April), Canc. Res., 55(3), 603-609 (1995) or AFMC Int. Med. Chem.

Symp. (1997) Abst. PB-55 (Seoul-27 July-1 August), the disclosure of each of these is incorporated herein by reference.

Camptothecin (CPT), an optically active (S configuration of the tertiary hydroxy group in the 20-position) cytotoxic alkaloid, was discovered by Wall in the late 1950s while screening for anti-proliferative natural products. Camptothecin has an anti-proliferative activity in several cancerous cell lines, including the cell lines of human tumors of the colon, lung and breast (Suffness, M et al: The Alkaloids Chemistry and Pharmacology, Bross A., ed., Vol, 25, p. 73 (Academic Press, 1985)). It is suggested that the anti-proliferative activity of camptothecin is related to its inhibitory activity on DNA topoisomerase I.

Numerous CPT analogs have been synthesized utilizing the information derived from the structure-activity relationships of CPT. The CPTs are known to possess antiangiogenic properties in addition to being cytotoxic agents. At a low dose (50 nM), which was not cytotoxic to normal human endothelial cells, CPT and Topotecan (TPT) inhibited the growth of human umbilical venular endothelial cells in vitro.

Semi-synthetic derivatives such as CPT-11 and TPT, are approved by the FDA for the treatment of many cancers, while the synthetic derivatives homocamptothecins and silatecan are undergoing clinical evaluation. These new analogs have improved lactone stability, which has been achieved by increasing the lipophilicity (silatecans) or by changing the lactone ring to a seven membered structure (homocamptothecins).

Irinotecan hydrochloride (CPT-11) [7-ethyl-10-(4-(1-piperidino)-1-piperidino)carboxycamptothecin] is a derivative of CPT in which the phenolic hydroxyl group of CPT is linked to a piperidino-piperidine through a carbamate bond. CPT-11 is commercially available as an intravenous injection (Camptosar®) and has received FDA approval as first line therapy for the treatment of colorectal cancer (FDA 2000).

Topotecan (TPT) (9-amino-dimethyl-10-hydroxycamptothecin) differs from CPT by two structural modifications: a (dimethylamino)methyl moiety at position 9 and a phenolic residue at position 10. These modifications confer water solubility and stability of the active lactone moiety. TPT is formulated as the water-soluble hydrochloride derivative (solubility: ~1 mg/mL), which is positively charged at physiological pH and exhibits improved lactone stability due to minimal affinity of the carboxylate form for albumin. TPT is commercially available for intravenous injection (Hycamtin®) and is approved as second-line therapy for metastatic ovarian cancer.

In an attempt to improve the stability of the lactone ring, a silyl group can be attached to position 7 in the silatecans, increasing the lipophilicity of the camptothecins. This results in limited drug inactivation by both protein binding and hydrolysis of the lactone moiety. Karenitecin and DB-67, are two of the leading members of this class.

Expansion of the E-ring of CPT to a seven membered β-hydroxylactone ring in the homocamptothecins further stabilizes the lactone ring and decreases protein binding. These compounds have been shown to induce DNA cleavage at additional sites. Two homocamptothecins, BN 80245 and BN 80915, exert greater antiproliferative activity than CPT and TPT.

Further modification of the homocamptothecins to include the attachment of a silyl-alkyl functionality at the 7-position have resulted in the formation of homosilatecans. These compounds display improved lipophilicity and stability in human whole blood.

These drugs (e.g., Camptothecins) are particularly preferred for use in accordance with the compositions of the present invention as the active lactone form of CPT (camptothecin) is stabilized in liposomes. Therefore, higher concentrations of the active drug can reach the tumor site, which may occur by extravasation through the pourous capillaries surrounding the tumor. In addition, encapsulation of camptothecins within liposomes preferably protects the campthothecins from secretory efflux by apically located efflux pumps, thus increasing intracellular accumulation.

In certain embodiments, wherein the therapeutically active agent is a member of the group of camptothecins described above, the compositions of the present invention are useful in the treatment of certain types of cancers. In particular the compositions of the present invention can be used for the treatment of tumors associated with certain types of cancers. Examples of tumors or cancers include cancers of the oesophagus, the stomach, the intestines, the rectum, the oral cavity, the pharynx, the larynx, the lung, the colon, the breast, the cervix uteri, the corpus endometrium, the ovaries, the prostate, the testicles, the bladder, the kidneys, the liver, the pancreas, the bone, the connective tissues, the skin, the eyes, the brain and the central nervous system, as well as cancer of the thyroid, leukemia, Hodgkin's disease, lymphomas other than those related to Hodgkin, multiple myelomas and others. In certain embodiments the composition provides the ability to produce a "multilog cell kill" that is required to induce tumor regression, by the continued administration of the camptothecin, salt thereof or analog thereof over a prolonged period of time, and preferably sparing normal hematopoietic calls and mucosal progenitor cells.

In certain embodiments, the compositions of the present invention prevent or limit tumor growth by preventing activation of angiogenesis or by directly targeting the vascular endothelial cells of the formed blood vessels of a tumor. In certain embodiments, the compositions of the present invention circumvent the problems of insufficient penetration into the interior of the tumor mass an avoids the necessity of having to obtain intra-tumor drug delivery.

With regard to therapeutically active agents, for long term therapy (days, weeks or months) and/or to maintain the highest possible drug concentration at a particular location in the body, the present invention in certain embodiments provides a sustained release depot formulation with the following preferred but non-limiting characteristics: (1) the process used to prepare the matrix does not chemically or physically damage the therapeutic agent; (2) the matrix and liposomes maintain the stability of a therapeutic agent against denaturation or other metabolic conversion by protection within the matrix and liposome until release, which is important for very long sustained release; (3) the entrapped therapeutic agent is released from the hydrogel composition at a substantially uniform rate, following a kinetic profile, and furthermore, a particular therapeutic agent can be prepared with two or more kinetic profiles, for example, to provide in certain embodiments, a loading dose and then a sustained release dose; (4) the desired release profile can be selected by varying the components and the process by which the matrix and liposomes are prepared; and (5) the matrix and liposomes are nontoxic and degradable.

In another related aspect, the delivering of at least one therapeutic agent to a bodily compartment under controlled release conditions is provided by situating in the bodily compartment a pharmaceutical formulation comprising a matrix as described hereinabove. The bodily compartment may be subcutaneous, oral, intravenous, intraperitoneal, intradermal, subdermal, intratumor, intraocular, intravisceral, intraglandular, intravaginal, intrasinus, intraventricular, intrathecal, intramuscular, or intrarectal, by way of non-limiting examples. The composition of the invention may be provided to the bodily compartment by a route such as but not limited to subcutaneous, oral, intravenous, intraperitoneal, intradermal, subdermal, intratumor, intraocular, intravisceral, intraglandular, intravaginal, intrasinus, intraventricular, intrathecal, intramuscular, or intrarectal. In certain preferred embodiments, the composition is provided to the bodily compartment by subcutaneous administration.

In certain embodiments, the invention is further directed to a method of preparing a cross-linked hydrogel drug depot, the method comprising: preparing a mixture comprising at least one therapeutic agent in a liposome or plurality of liposomes and a polymer system capable of forming a cross-linked hydrogel matrix, the polymer system comprising a first polymer having a plurality of functional groups, and a second polymer or long-chain compound having two or more functional or reactive groups; and forming linkages between the functional groups of the first polymer and the functional or reactive groups of the second polymer so as to form a cross-linked hydrogel matrix entrapping the liposome or plurality of liposomes and the therapeutic agent physically entrapped within the liposomes or liposomes. The first and second polymer may be the same or different. The first or second polymer may be a polyalkylene oxide, and either or both may be a homopolymer, a copolymer or a combination thereof. They may have one or more biodegradable linkages. In a preferred embodiment, one polymer comprises thiol groups and the other comprises vinylsulfone or maleimide groups. Reaction of the vinylsulfone or maleimide groups with the thiol groups forms cross-links. In another embodiment, the first and second polymers comprise thiol groups, and a homobifunctional thiol-reactive cross-linking agent is used to form cross-links. In these examples, the plurality of thiol groups may be between 2 and 20. The second polymer may be a long-chain cross-linking agent.

In certain embodiments to prepare the polymer on which at least two thiol groups are present from these reactants, the thiol group of thiomalic acid is first protected by reaction with trityl chloride, to produce trityl-thiomalic acid. Subsequently, the polymer on which at least two thiol groups are present is prepared from the trityl-thiomalic acid and, for example, $\alpha,\omega$-dihydroxy-PEG. Under suitable conditions, a carbodiimide is used to condense the $\alpha,\omega$-dihydroxy-PEG with the protected thiomalic acid. After condensation, the trityl group is removed by treatment with trifluoroacetic acid (TFA).

In certain other embodiments, a polymer of $\alpha,\omega$-dicarboxy-PEG and lysine may be prepared, and subsequently the free carboxy groups on the lysine residues are derivatized to form thiol groups. These examples are provided by way of illustration only and such methods for adding thiol groups to a polymer are known to those skilled in the art.

The releasing of a therapeutically effective amount of the therapeutic agent from the cross-linked hydrogel matrix may occur over a time course of three or more, five or more, ten or more, fifteen or more, or twenty or more days. Release of weeks to months by the compositions of the invention is also embraced herein. The controlled release profile may comprise a desired initial bolus release profile followed by a release profile such as but not limited to zero order, pseudo zero order, and first order.

In certain embodiments, the formulation further comprises one or more excipients that modulate one or more properties of the cross-linked matrix, such as swelling of the polymer. Such excipients include, by way of non-limiting example, mono- or divalent metal ions, anions or ionic polymers, proteins such as serum albumin, surfactants and polymers such as dextran. Moreover, components may be added to the formulation to provide enhanced stability of any therapeutic agents contained therein.

Preferably the controlled release of the at least one therapeutic agent from the pharmaceutical formulation of the invention occurs as a consequence of diffusion from the liposome(s) and from the matrix wherein the liposome(s) is (are) dispersed. Preferably the presence of liposome beneficially influences the controlled release characteristics of the active agent in the composition. Moreover, the ratio among the aforementioned types of stable and labile cross-linking bonds, among other factors, may be used to regulate the persistence of the composition within the body and the release kinetics of the liposome entrapped therapeutic agents. For example, in certain embodiments, a ratio of thioether, thioester and disulfide bonds may provide the proper release pharmacokinetics for a composition of the invention placed in a particular bodily site that is exposed to esterases as well as reducing activity.

Preferably, the active agent of the compositions of the present invention is delivered to a particular site within the body using the methods described herein, for sustained delivery to target cells or tissues. In certain embodiments, the judicious placement of the matrix of the present invention will permit targeted delivery to a particular site within the body, and furthermore, allow a higher concentration of the therapeutic agent to contact a particular site than achievable if the same therapeutic agent is administered systemically. In particular, administration of an agent which induces apoptosis in dysproliferative conditions, such as a tumor, may be performed by the placement (herein termed administration) of the matrix in the proximity of the tumor, thus delivering the therapeutic agent proximal to the tumor. The same strategy is used for proximal delivery of therapeutic agents to other particular body sites or compartments, such as for example and without limitation, through the skull into the brain.

A subject in whom administration of the pharmaceutical composition of the present invention is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The invention is also directed to a kit for forming a hydrogel formulation comprising a therapeutic agent incorporated into a liposome or plurality of liposomes and a polymer with two or more functional groups, and a cross-linking agent capable of forming a cross-links among the functional groups. In the use of the kit, the liposomes or liposomes including the therapeutic agent is added to the polymer and cross-linking agent and cross-linking is induced, in accordance with one of the aforementioned processes of forming the matrix in vitro, or forming it in situ by injecting the components soon after mixing, such that the matrix is not yet polymerized and can pass through a needle or cannula, and full cross-linking occurs in situ.

The present invention will now be more fully described with reference to the accompanying examples. It should be understood, however, that the following description is illustrative only and should not be taken in any way as a restriction on the invention specified above.

Example 1

In Example 1, a hydrogel formulation in accordance with the present invention was prepared as follows:

A. Synthesis of Thiol Protected 2-Mercaptosuccinic Acid.

One equivalent of 2-mercaptosuccinic acid and three equivalents of triphenylmethyl (trityl) chloride were dissolved in degassed dimethyl formamide (DMF) in a flask assembled with an argon balloon. The reaction was performed at room temperature (25° C.) with magnetic stirring overnight and monitored by thin layer chromatography. The reaction mixture was extracted in dichloromethane (DCM) and loaded onto a silica gel column for purification. The eluted fractions containing trityl-protected mercaptosuccinic acid were collected and dried using rotary vacuum evaporation (Buchi RE111 Rotavapor, Brinkman Instruments Inc. Westbury, N.Y.) followed by high vacuum (Welch W oil pump, Series 5, Welch Rietschle Thomas, Skokie, Ill.). The product was characterized using mass spectroscopy.

B. Synthesis of the Thiol-Containing PEG Copolymer.

A thiol-containing PEG-based copolymer was synthesized using a solution polymerization technique as described by Qiu et al., "A hydrogel prepared by in situ cross-linking of a thiol-containing poly(ethylene glycol)-based copolymer: a new biomaterial for protein drug delivery," *Biomaterials*, 24:11-18, the disclosure of which is hereby incorporated by reference in its entirety. In a flask assembled with an argon balloon equivalent molar quantities of α,ω-diamino-poly(ethylene glycol) (MW 3400 Da) and trityl-mercaptosuccinic acid, 0.5 equivalents of 4-(dimethyl amino) pyridine (DMAP) and 0.5 equivalents of p-toluenesulfonic acid monohydrate (PTSA) were dissolved in dichloromethane (DCM). The reaction mixture was cooled to 0° C. in an ice-water bath after which 3.5 equivalents of 1,3 diisopropylcarbodiimide (DIPC) were added. The temperature was maintained at 0° C. for one hour and then increased to 25° C. to perform direct polymerization.

After 5 days the reaction mixture was precipitated in ten volumes of ice-cold diethyl ether to recover the polymer product. The polymer was dialysed (Spectra/Por membrane MW cut off (MWCO) 12 000 Da) against water for 24 hours with three volume changes to remove any low molecular weight polymers and lyophilized. The lyophilized polymer was then treated with trifluoroacetic acid (TFA, 90%), thioanisole (5%), EDT (3%) and anisole (2%) for 2 hours to remove the protecting trityl groups from the polymer pendent sulfur atoms. The deprotected polymer was precipitated in ice-cold diethyl ether, washed five times with ice-cold diethyl ether and dried under vacuum. The resulting thiol-containing PEG copolymer was stored under argon at −20° C.

C. Preparation of the Hydrogel Through Chemical Cross-Linking

Stoichiometric amounts of the PEG-based copolymer and a sulfur-containing cross-linking reagent, that was reactive with the copolymer sulfhydryl groups, were dissolved separately in phosphate buffer saline (PBS). The drug to be physically entrapped in the hydrogel was dissolved or suspended in either solution. Upon mixing of the two solutions the viscosity increased resulting in the formation of a transparent hydrogel.

Example 2

In Example 2, TPT-liposomes were prepared by active loading. "Active loading" of drugs in liposomes typically includes the generation of Transmembrane pH gradients in which the liposomal interior pH is such that once the unionized drug passively diffuses into the liposome it becomes charged and thus trapped in the liposome interior.

A. Transmembrane pH Gradient

TPT liposomes were prepared by dissolving DSPC (3.8 µmoles), cholesterol (25 µmoles) and egg phosphatidyl choline (9.2 µmoles) in chloroform. The organic solvent was completely removed by rotary evaporation and high vacuum forming a thin lipid film. The lipid film was hydrated with 4 mL PBS (0.1 M, pH 8.0) for 90 minutes with constant agitation while maintaining a temperature of 60° C. The liposome suspension was sonicated for 60 minutes to reduce the size of the liposomes. The external pH was reduced to 2 units with HCl (1.0 M) generating a transmembrane gradient in which the internal pH of the liposomes was 8.0 and the external pH was 2.0. Active loading was performed by adding a solution of TPT (11.2 mg dissolved in 200 µL PBS 0.1 M, pH 3.0) to the liposome suspension which was maintained at 60° C. and vortexed every 10 minutes for one hour. The liposomal suspension was repeatedly extruded through filters of decreasing pore (1 µm to 0.05 µm) using the Liposo-Fast 50 system. Untrapped drug was removed by passing the liposome suspension through a gel filtration column (Sephadex G50) which was equilibrated with PBS (0.1 M, pH 3.0) and collecting the void volume. The liposomes were stored at 4° C.

B. Transmembrane Ionic Gradient

Creating a pH gradient across the liposome membrane as described above may not facilitate complete loading of the drug into the liposomes since the buffer capacity may be insufficient to maintain the pH gradient during the loading process. Transmembrane ionic gradients generated with ammonium sulfate or calcium acetate have been reported to increase drug loading as the pH gradient they create is maintained over a longer time period. DSPC (12 µmoles) and cholesterol (8 µmoles) were dissolved in chloroform which was evaporated to dryness forming a thin lipid film. The flask was stored under vacuum overnight to remove all traces of organic solvent. The lipid film was hydrated with 2 mL of ammonium sulfate (0.25 M, pH 5.0) and agitated for 2 hours using rotary evaporation. Glass beads (diameter=3 mm) were added to the flask to increase the degree of mixing. The liposome aqueous dispersion was then sonicated for 10 minutes and freeze-thawed in liquid nitrogen five times to reduce the liposome size. A homogeneous liposome suspension was prepared by repeatedly extruding the liposomes at 60° C. through polycarbonate membrane filters of decreasing pore size using the Liposo-Fast 50 system. The external buffer was changed by passing the liposome suspension through a Sephadex G-50 column equilibrated with Mes buffer (0.1 M, 2 mM EDTA, pH 5.5). TPT (2 mg) was added to the liposome suspension which was agitated for 30 minutes at 60° C. After loading, the untrapped drug was removed by Sephadex G50 gel filtration in 0.9% NaCl (pH 6.0, 286 mOs) and the liposomes were stored at 4° C.

Example 3

Release of Free TPT and TPT-Liposomes from the Hydrogel

Hydrogels containing 4% (w/v) copolymer were prepared as described in Example 1. Free TPT (238 μg/gel) or TPT liposomes (238 μg/gel) were added to the copolymer solution and physically entrapped in the hydrogel upon the addition of the vinylsulfone crosslinker (PEGDVS). Hydrogels were either placed directly in vials containing 15 mL of release buffer (PBS 0.1 M, pH 7.4) or in dialysis bags (containing 1 mL of buffer), which were subsequently submerged in vials of PBS. At predetermined time intervals, an aliquot was removed from each vial and the concentration of TPT determined fluorometrically. To ensure that sink conditions were maintained, an equivalent volume of release buffer was replaced after sampling.

To distinguish between whether free TPT or intact TPT liposomes were released from the hydrogel, hydrogels containing TPT liposomes were either placed directly in the release buffer (total drug released) or placed in a dialysis bag (MWCO 3000) (free TPT released) which was submerged in release buffer. To ensure that binding of TPT to the dialysis tubing did not occur, hydrogels loaded with free TPT were also either placed directly in the release buffer or in a dialysis bag (MWCO 3000) which was submerged in release buffer.

Results

TPT did not bind to the dialysis bag as the release profiles of free TPT were similar irrespective of whether the hydrogel was first placed in a dialysis bag or not. Therefore, the permanent entrapment of liposomes within the hydrogel could be the reason that not all of the drug was released.

Physically entrapping TPT loaded liposomes in the hydrogel prolonged the release period of the drug from the hydrogel 60 fold compared to that of free drug in the hydrogel. Intact TPT liposomes were slowly released from the hydrogel since their movement along the tortuous pathways in the hydrogel was restricted due to the similarity between their size and that of the pores in the hydrogel. The release of free TPT from the hydrogel was also impeded as the drug encountered two barriers, the lipid bilayer of the liposomes and the polymer chains within the hydrogel, prior to being released into the medium. Since TPT liposomes are relatively unstable at 37° C., it was not possible to determine the fraction of free TPT and intact liposomes that were released from the hydrogel. It is possible that free TPT could leak from intact liposomes that are either still entrapped in the hydrogel or released from the hydrogel over time. Nevertheless, prolonged release of the low molecular weight water-soluble drug, TPT, was achieved from the hydrogel using a two phase system.

Example 4

Cell Culture Models

The human ovarian carcinoma cell lines, A2780 (sensitive) and A2780/AD (multidrug resistant), were obtained from Dr. T. C. Hamilton (Fox Chase Cancer Center, Pa.). A2780/AD is a multidrug resistant cell line that expresses the MDR1 gene encoding P-glycoprotein. The breast cancer cell line, Mat B-III, syngeneic with Fisher 344 rats, was obtained from American Type Culture Collection. The cells were cultured in RPMI media supplemented with 10% fetal bovine serum, 100 units/ml penicillin-streptomycin sulfate, 2% sodium bicarbonate and 1% non-essential amino acids. Cells were grown at 37° C. in a humidified atmosphere of 5% $CO_2$ (v/v) in air. All experiments were performed on cells in the exponential growth phase.

A. In Vitro Cytotoxicity

The cytotoxicity of free TPT and liposome encapsulated TPT on A2780 and A2780/AD cells was assessed using a modified MTT (3-(4,5-dimethylthiazol-2-yl 2,5-diphenyltetrazolium bromide) assay. Cells in the exponential growth phase were harvested with trypsin ethylenediaminetetraacetic acid 1×, washed and seeded on 96-well plates at a density of 10,000 cells per well. The cells were allowed to attach for 24 hours. A concentration range (12 dilutions) of various treatments was applied to the cells (free drug, drug entrapped in liposomes, blank liposomes and blank liposomes coincubated with free drug) for 48 hours. On completion of the study, cell viability was determined by the addition of 25 μL of MTT (5 mg/ml dissolved in PBS) for 5 hours at 37° C.

MTT is cleaved by the active mitochondrial dehydrogenase which is present in viable cells. This results in the formation of blue/purple crystals which were dissolved by the addition of sodium dodecylsulfate (20.9 g dissolved in 50:50 DMF:water). The color intensity of each well was read at 570 nm with a reference wavelength of 690 nm. Cells not exposed to drug were designated as control cells (100% viability). The cellular viability of each drug treatment was calculated by comparing the intensity of that well to those of the control wells. The IC50 for each treatment was calculated as the concentration at which 50% of the cells are viable. The resistance index which is the ratio between the 50% growth inhibition obtained in the resistant cells to that obtained in the sensitive cells was calculated for the various treatments. This index represents the extent to which cells are resistant to an anticancer drug when compared to their sensitive counterparts.

Results

The cytotoxicity of liposome encapsulated TPT was determined in the above cells and compared to that of free drug. In A2780 cells the difference in the IC50 values for TPT and TPT liposomes was minimal (25.32±1.4 nM vs 18.8±0.9 nM). However, in the resistant cell line (A2780/AD) the IC50 values are significantly different (TPT: 55.89±2.67 nM, TPT liposomes: 38.57±2.87 nM). This decrease in the IC50 value could be attributed to circumvention of the apically located secretory efflux pumps by the TPT encapsulated drug. To confirm this, cells were preincubated and co-incubated with the Pgp and BCRP specific inhibitor, GF 120918 (2 μM), prior to incubation with the drug. The IC50 values were not significantly different in the presence of GF 120918. This indicates that either another efflux transporter is responsible for the observed difference in the IC50 values between free TPT and liposomal TPT in A2780/AD cells or that liposomal encapsulation of TPT facilitates drug uptake by fusing with the cell membrane, thus largely circumventing the efflux mechanism. Cytotoxicity of the TPT formulations in Sensitive (A2780) and Resistant (A2780/AD) Human Ovarian Carcinoma cells is listed in Table 1 below:

TABLE 1

Cytotoxicity of the TPT formulations in Sensitive (A2780) and Resistant (A2780/AD) Human Ovarian Carcinoma cells

| Formulation | IC$_{50}$ (nM) A2780 | IC$_{50}$ (nM) A2780/AD | Resistance Ratio |
|---|---|---|---|
| TPT | 25.32 ± 1.40 | 55.89 ± 2.67 | 2.21 |
| TPT-Liposomes | 18.80 ± 0.99 | 38.57 ± 2.51 | 2.05 |
| TPT + GF 120918 | 21.28 ± 1.04 | 52.58 ± 3.62 | 2.47 |
| TPT-Liposomes + GF 120918 | 23.03 ± 1.64 | 38.13 ± 2.87 | 1.66 |
| TPT + Liposomes | 31.51 ± 0.78 | 38.93 ± 1.54 | 1.23 |

Resistance ratio = IC$_{50}$ (resistant cells)/IC$_{50}$ (sensitive cells)

Example 5

Pharmacokinetic Evaluation of the Controlled Release Formulations

Clinical studies have indicated that the pharmacodynamics of TPT are more consistent with the plasma area under the curve (AUC) of total drug than with that of the lactone form alone. Therefore, the total drug was analysed in the pharmacokinetic studies. In Example 5, Jugular vein catherized female Fischer 344 rats purchased from Hilltop Laboratories (Scottdale, Pa.) were used to investigate the pharmacokinetics and pharmacodynamics of the various TPT formulations. Rats, aged 2-6 months and weighing 300 g-350 g were housed in individual cages with free access to food and water. The rats were allowed to acclimate for a week. All animals studies were conducted in accordance with the protocol approved by Laboratory Animal Services (LAS), Rutgers University (Protocol No: 03 003).

A. Drug Administration

TPT solution for intravenous (i.v.) and subcutaneous (s.c.) injection was prepared by dissolving TPT (5 mg) in 0.5 mL of acidified sterile saline (pH 2.5). Since the lactone form of TPT is essential for cytotoxic activity, it is advisable to administer TPT dissolved in an acidic medium (at pH<3.5 100% of the drug is present in the lactone form). TPT loaded hydrogels (4% w/v) were prepared by homogeneously suspending TPT (5 mg/mL in sterile phosphate buffer, 0.1 M, pH 7.4) in the copolymer solution followed by the addition of the vinylsulfone crosslinker (PEGDVS). The pH of the solutions was adjusted to 7.4 such that a gelation time of 3 to 4 minutes was achieved. TPT liposomes were prepared as described in e.g., Example 2B, except that the final extraction of the liposome suspension was performed using phosphate buffer (0.1 M, pH 7.4). The final concentration of TPT in the liposomes was adjusted to 5 mg/mL by appropriate dilution. Hydrogels (4% w/v) loaded with TPT liposomes were prepared by dissolving stoichiometric amounts of the copolymer and cross-linker in the liposome suspension prior to mixing them together and injecting subcutaneously.

In the pharmacokinetic evaluation of the various formulations of TPT a dose of 10 mg/kg was selected to ensure adequate detection.

Five groups, each consisting of four rats, were used to investigate the pharmacokinetics of the TPT formulations. Group A received a single i.v. bolus dose of TPT (10 mg/kg). The drug solution (0.3 mL) was administered slowly via the tail vein. An equivalent dose of TPT (10 mg/kg) was administered s.c. into the back of the rats in Group B. Free TPT physically entrapped in the hydrogel (0.6 mL) was administered s.c. prior to gelation in Group C. Group D received a s.c. injection of TPT-liposomes (0.6 mL) and Group E received a s.c. injection of TPT-liposomes physically entrapped in the hydrogel (0.6 mL).

Blood samples (0.2 mL) were collected from the jugular vein at 0, 5, 15, 30 min, 2, 4, 6, 8, 12, 24 h after drug administration for Groups A, B and C. For Group D additional blood samples were withdrawn at 48 and 72 h after drug dosing and for Group E the following sampling points were used: 0, 15, 30 min, 2, 4, 6, 8, 12, 24, 48, 72, 98 and 168 h after drug administration. After 24 hours the jugular catheters were disconnected from the sampling ports and plugged to allow the rats to move around freely. The plasma samples were immediately separated after centrifugation (16,000 g for 10 minutes at 4° C.) and frozen at −20° C. until analysis.

B. Results

1. Model-Independent Analysis

The pharmacokinetics of the various TPT formulations were determined in female Fischer 344 rats. To facilitate comparison of all the formulations, the plasma-concentrations profiles were first analyzed using a model independent approach. The pharmacokinetic parameters obtained are listed in Table 2. The following parameters, area under the plasma concentration-time curve (AUC), clearance (Cl), time to reach peak plasma concentration ($t_{max}$), peak plasma concentrations ($C_{max}$), terminal rate constant ($k_{el}$), elimination half-life ($t_{1/2}$) and mean residence time (MRT) were used to compare the various formulations. The area under the plasma concentration-time curve from zero to infinity ($AUC_{0\rightarrow\infty}$) was calculated using the log-linear trapezoidal method up to the last measured concentration time point with extrapolation to infinity using the terminal rate constant $k_{el}$. The terminal phase of the logarithm of the plasma concentration time profile was visually selected and kel was estimated by linear regression. The absolute bioavailability was calculated as the ratio of the $AUC_{0-\infty}$ after extravascular administration divided by the $AUC_{0-\infty}$ after i.v. administration.

Figure 1B:
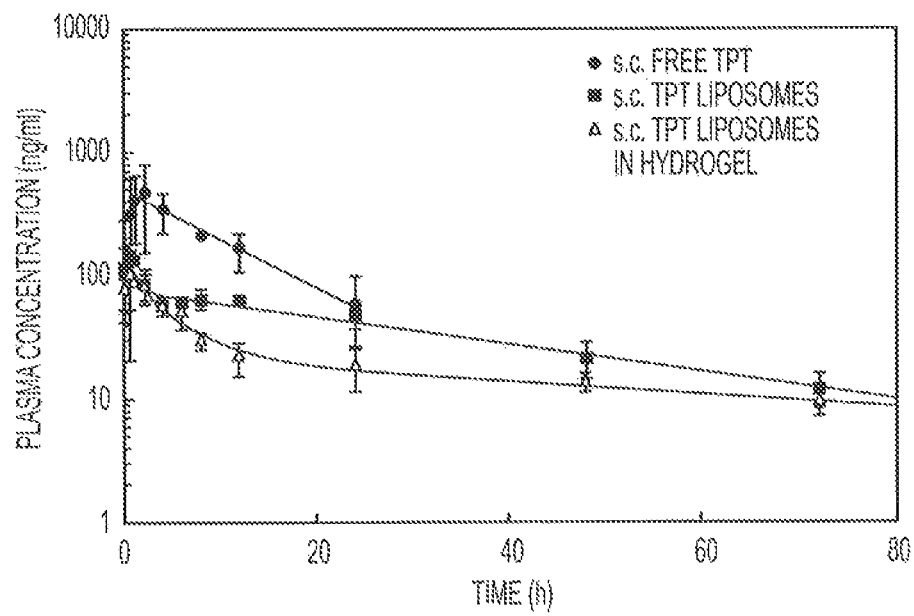

The $C_{max}$ after intravenous administration of TPT was 10-fold greater than that after subcutaneous injection of TPT. This high initial concentration may be responsible for the toxicity of these drugs. The Cmax following the s.c. administration of TPT solution and that of TPT in the hydrogel were similar (468.18±177.36 vs 641.23±107.52 ng/ml) and 5-fold greater than that after the administration of TPT liposomes and TPT liposomes in the hydrogel (141.13±17.32 vs 100.41±8.05 ng/ml) (FIG. 1). The lower $C_{max}$ achieved suggests that these delivery systems may be safer than the administration of TPT solution. The AUC was similar following the i.v. administration of the TPT solution, the s.c. injection of the TPT solution and TPT in the hydrogel. Therefore, these formulations are equally effective as drug exposure is similar. However, the lower $C_{max}$ and increase in MRT following the s.c. administration of TPT solution and TPT in the hydrogel results in an increase in duration of response.

The elimination half-life ($t_{1/2}$) was similar following i.v. and s.c administration of TPT solutions and TPT in the hydrogel but was substantially longer following s.c. administration of TPT liposomes and liposomes entrapped in the hydrogel. These observations indicate that the appearance of TPT from the s.c. site to the central compartment following the administration of TPT liposomes and liposomes in hydrogel occurs slowly confounding the elimination kinetics. This was confirmed by the increase in the MRT. The mean absorption time (MAT) of the TPT solution and the mean dissolution time (MDT) of TPT liposomes after s.c. injection can be estimated using the following equations:

other formulations with all rats maintaining their body weight throughout the observation period. The administration of TPT via the i.v. or s.c. routes may not be effective as a result of their rapid clearance. Therefore, liposomes entrapped in the hydrogel are a promising strategy for the controlled delivery of S-phase anticancer agents.

TABLE 2

Non-compartmental analysis of pharmacokinetic data of TPT

| | | Mean (±SE) | | | | |
|---|---|---|---|---|---|---|
| Parameters | Units | i.v. TPT | s.c. TPT | s.c. TPT Hydrogel | s.c. TPT Liposomes | s.c. TPT LS/HG* |
| $AUC_{0-\infty}$ | $h \cdot ng \cdot mL^{-1}$ | 5906.61 (±855.34) | 5383.02 (±593.06) | 6724.22 (±409.45) | 3121.61 (±429.84) | 3585.24 (±358.05) |
| $AUC_{0-t}$ | $h \cdot ng \cdot mL^{-1}$ | 5794.31 (±865.06) | 4465.37 (±342.39) | 6701.81 (±406.60) | 2665.06 (±272.84) | 2340.71 (±201.79) |
| Cl/F | $mL \cdot h^{-1}$ | 444.59 (±47.21) | 473.25 (±50.43) | 391.15 (±24.67) | 650.41 (±87.22) | 734.09 (±90.38) |
| Cl | $mL \cdot h^{-1}$ | 444.59 (±47.21) | 434.44 (±46.29) | 427.14 (±26.94) | 440.33 (±59.06) | 439.72 (±54.14) |
| $C_{max}$ | $ng \cdot mL^{-1}$ | 4355.26 (±450.69) | 468.18 (±177.36) | 641.23 (±107.52) | 141.13 (±17.33) | 100.41 (±8.05) |
| $k_{el}$ | $h^{-1}$ | 0.14 (±0.03) | 0.10 (±0.03) | 0.13 (±0.00) | 0.03 (±0.00) | 0.01 (±0.00) |
| MRT | h | 2.95 (±0.44) | 13.39 (±4.27) | 9.19 (±1.59) | 36.27 (±4.36) | 143.51 (±12.66) |
| $t_{1/2}$ | h | 5.45 (±0.87) | 9.16 (±2.99) | 5.46 (±0.14) | 24.50 (±3.18) | 91.12 (±17.70) |
| $V_{ss}$ | mL | 1320.09 (±277.90) | | | | |
| $V_z/F$ | mL | 3552.68 (±808.25) | 5973.59 (±1528.81) | 3074.62 (±128.59) | 22191.85 (±236.64) | 93878.43 (±19472.02) |
| $V_z$ | mL | 3552.68 (±808.25) | 5483.75 (±1403.45) | 3357.49 (±140.42) | 15023.89 (±160.20) | 56233.18 (±11663.74) |
| $t_{max}$ | h | | 2.67 (±0.67) | 5.33 (±1.33) | 0.33 (±0.08) | 0.44 (±0.06) |
| MAT | h | | 10.44 | 6.24 | 33.32 | 140.56 |
| MDT | h | | | 0 | 22.88 | 130.12 |

*LS/HG: Liposomes entrapped in Hydrogel $$MAT=MRT_{s.c.}(\text{TPT solution/liposomes})-MRT_{i.v.}(\text{TPT solution})$$

$$MDT=MRT_{s.c.}(\text{TPT liposomes})-MRT_{s.c.}(\text{TPT solution})$$

The MAT of s.c. TPT solution and liposomes was 10.44 and 33.32 h, respectively, indicating that the rate at which TPT appears in the central compartment is slower with liposomal TPT than with TPT solution. Similarly, the MAT of TPT liposomes in the hydrogel, compared to that of TPT liposomes, was significantly greater (140.56 vs 33.32 h) confirming that the appearance of drug in the central compartment is much slower as the drug has to diffuse through two barriers; the liposome membrane and the hydrogel prior to being released into the s.c. tissue. The MDT, which reflects the time for the TPT liposomes to release drug in vivo, was 22.88 h for TPT liposomes and 130.12 h for TPT liposomes in the hydrogel. Entrapping TPT liposomes in the hydrogel stabilized them and prolonged the release period of free drug from the hydrogel into the s.c. site. The longer MDT represents controlled release of TPT from the liposomes and from the hydrogel in vivo.

Figure 2:
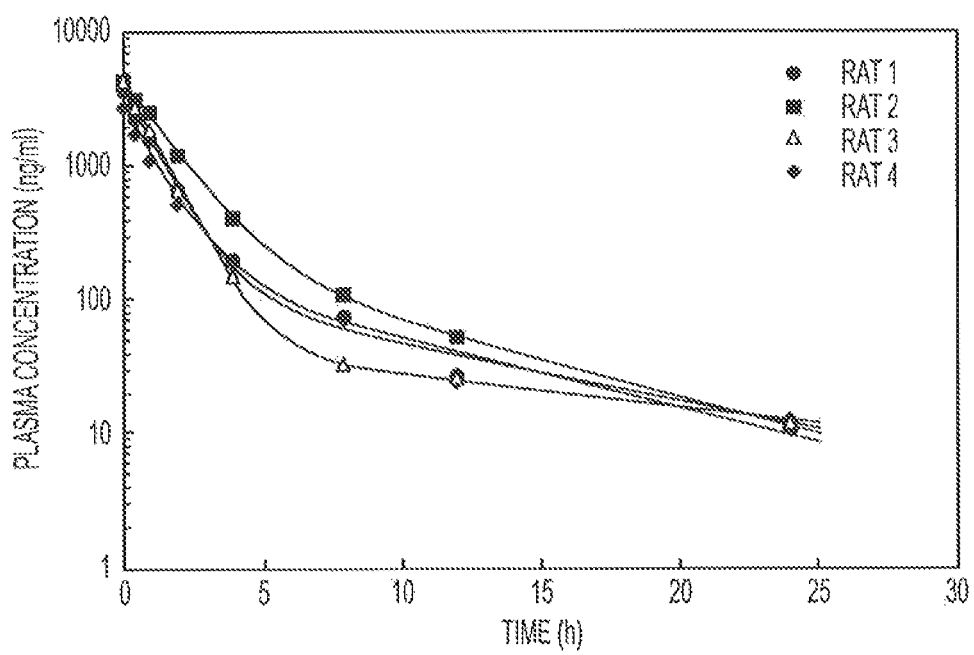
FIG. 2: Graphically depicts plasma concentration-time profile of topotecan after intravenous administration (10 mg/kg) in Fischer 344 rats. TPT solution (5 mg/ml in acidified normal saline pH 2.56) was injected via the tail vein and samples were withdrawn via the catheterized jugular vein.

Since the mean TPT plasma levels were maintained above 10 ng/mL for extended periods, the liposomes in hydrogel formulation demonstrated an advantage over the other methods of administering TPT to achieve controlled release (FIG. 1). In addition, the liposomes in hydrogel formulation was well tolerated at the dosage administered compared to the 2. Model-Dependent Analysis a. Intravenous (i.v.) Administration of TPT The plasma profile of TPT following i.v. administration was shown to best fit an open two-compartment model (Equation 5.1), where the drug-plasma concentrations declined biphasically (FIG. 2). The estimated model parameters are reported in Table 3.

$$C_p=Ae^{-\alpha t}+Be^{-\beta t} \quad \text{Equation 5.1}$$

$C_p$=concentration of drug in plasma

A=y intercept for the distribution phase

B=y intercept for the elimination phase

α=distribution rate constant

β=elimination rate constant t=time

TPT undergoes rapid distribution into the tissues. This is evident from the short distribution half-life (distribution half life; alpha-t½=0.84±0.07 h) and large volume of distribution (Vss=1790.14±348.83 mL). The initial distribution rate is more rapid than the elimination rate (alpha=0.84 $h^{-1}$, beta=0.11 $h^{-1}$) and the relative area of the distribution phase is greater than that of the elimination phase (A/alpha=4421.42, B/beta=1284.06). Therefore, a significant portion of drug elimination occurs during the distribution phase.

The relatively high plasma clearance of TPT (Cl=453±57.02 mL/h) and short elimination half life ($t_{1/2}$=6.16±0.56 h) make the i.v. route of administration of TPT impractical for long-term therapy.

b. Subcutaneous (s.c.) Administration of TPT

Figure 3:
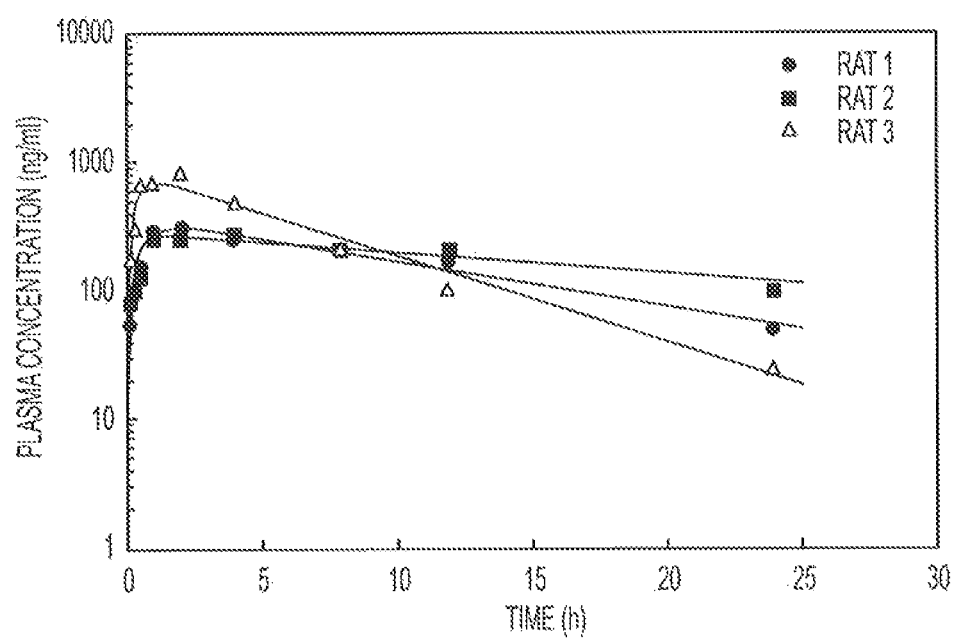
FIG. 3: Graphically depicts plasma concentration-time profile of topotecan after subcutaneous administration (10 mg/kg) in Fischer 344 rats. TPT solution (5 mg/ml in acidified normal saline pH 2.56) was injected and samples were withdrawn via the jugular vein.

The subcutaneous administration of a TPT solution produced a plasma profile that was best fit to a one-compartment model with first-order absorption and elimination (Equation 5.2) (FIG. 3). The estimated model parameters are reported in Table 3.

$$C_P = C_o e^{-k_{el} * t} \quad \text{Equation 5.2}$$

$C_p$=concentration of drug in plasma
$C_o$=initial drug concentration at zero time
$k_{el}$=elimination rate constant
t=time

TABLE 3

Compartmental analysis of pharmacokinetic data of TPT

| Parameter | Units | Mean (±SE) | | | | |
|---|---|---|---|---|---|---|
| | | i.v. | s.c. | s.c. Hydrogel | s.c. TPT Liposomes | s.c. TPT LS/HG* |
| A | ng · mL$^{-1}$ | 3730.35 (±439.19) | | | 119.30 (±28.17) | 122.08 (±28.59) |
| Alpha | h$^{-1}$ | 0.84 (±0.06) | | | 1.00 (±0.18) | 0.28 (±0.05) |
| Alpha-$t_{1/2}$ | h | 0.84 (±0.07) | | | 0.72 (±0.13) | 2.70 (±0.48) |
| $K_a$ | h$^{-1}$ | | 2.31 (±0.35) | 0.52 (±0.10) | 13.22 (±5.12) | 5.29 (±1.66) |
| $K_a$-$t_{1/2}$ | h | | 0.32 (±0.05) | 1.45 (±0.29) | 0.07 (±0.02) | 0.17 (±0.04) |
| AUC | h · ng · mL$^{-1}$ | 5955.13 (±820.97) | 5798.26 (±893.99) | 6788.76 (±547.43) | 3560.46 (±509.67) | 2954.83 (±455.40) |
| B | ng · mL$^{-1}$ | 146.05 (±42.92) | | | 70.07 (±4.56) | 20.60 (±2.67) |
| Beta/$k_{el}$ | h$^{-1}$ | 0.11 (±0.01) | 0.12 (±0.07) | 0.13 (±0.00) | 0.02 (±0.00) | 0.01 (±0.00) |
| $t_{1/2}$ | h | 6.16 (±0.46) | 6.42 (±1.99) | 5.53 (±0.12) | 35.06 (±6.10) | 89.25 (±15.62) |
| Cl/F | mL · h$^{-1}$ | 453.00 (±57.02) | 448.95 (±64.97) | 389.71 (±32.66) | 574.74 (±89.30) | 923.95 (±148.74) |
| Cl | mL · h$^{-1}$ | 453.00 (±57.02) | 443.56 (±64.19) | 429.46 (±36.00) | 443.70 (±68.94) | 455.51 (±73.33) |
| $C_{max}$ | ng · mL$^{-1}$ | 3876.40 (±437.84) | 431.65 (±137.92) | 530.64 (±32.55) | 144.39 (±17.52) | 106.86 (±13.03) |
| $t_{max}$ | h | | 1.56 (±0.22) | 3.74 (±0.46) | 0.23 (±0.06) | 0.70 (±0.10) |
| MRT | h | 3.92 (±0.61) | | | | |
| $V_{ss}/F$ | mL | 1790.14 (±348.83) | 6074.73 (±1655.50) | 3100.91 (±201.17) | 9680.53 (±1265.58) | 21525.37 (±4278.33) |
| V | mL | 1790.14 (±348.83) | 6601.83 (±1635.63) | 3417.20 (±221.69) | 7473.37 (±977.03) | 10612.00 (±2109.22) |

*LS/HG: Liposomes in Hydrogel

The dose fraction (F) of TPT that appeared in the systemic circulation after s.c. injection of the TPT solution, was found to be 92% (Table 4). The rate constant of the elimination phase ($k_{el}$) of the s.c injection was similar to that after intravenous injection. The absorption rate is greater than the elimination rate ($k_a$=2.31 h$^{-1}$, $k_{el}$=0.12 h$^{-1}$) therefore, TPT rapidly appears in the central compartment (absorption half-life, $t_{1/2}$(ka)=0.32±0.05 h) and does not confound the elimination kinetics. This is confirmed by the short $t_{max}$. Table 4 lists the bioavailability results for the TPT formulations.

TABLE 4

Bioavailability of TPT formulations

| Route of Admin. | Dose (mg) | Non Compartmental Analysis | | | Compartmental Analysis | | |
|---|---|---|---|---|---|---|---|
| | | AUC (h · ng · ml$^{-1}$) | AUC ± SE | F* | AUC (h · ng · ml$^{-1}$) | AUC ± SE | F* |
| i.v. TPT | 2.505 | 5906.611 | 855.342 | 1.000 | 5955.126 | 820.969 | 1.000 |
| s.c. TPT | 2.488 | 5383.024 | 593.057 | 0.918 | 5798.257 | 893.991 | 0.988 |
| s.c. TPT hydrogel | 2.612 | 6724.217 | 409.452 | 1.092 | 6788.756 | 547.430 | 1.102 |
| s.c. TPT liposomes | 1.956 | 3121.605 | 429.843 | 0.677 | 3560.458 | 509.668 | 0.772 |
| s.c. LS/HG** | 2.540 | 3585.237 | 358.055 | 0.599 | 2954.828 | 455.398 | 0.493 |

*F = (AUC$_x$*D$_{iv}$)/AUC$_{iv}$*D$_x$)
**LS/HG = Liposomes in hydrogel

FIG. 1 illustrates the concentration-time profile of TPT solution during the first 24 hours following i.v. and s.c. administration. Most of the administered drug appeared in the central compartment and was eliminated during the first 24 hours. The elimination phase for TPT from these two routes of administration was found to be similar. However, the $C_{max}$ after the s.c. administration of TPT was 9-fold lower than that following i.v. administration of TPT solution while the AUCs were similar. Therefore, drug exposure via the two routes is similar however the s.c route is possibly less toxic due to the lower $C_{max}$.

c. Subcutaneous (s.c.) Administration of TPT Entrapped in the Hydrogel

Figure 4:
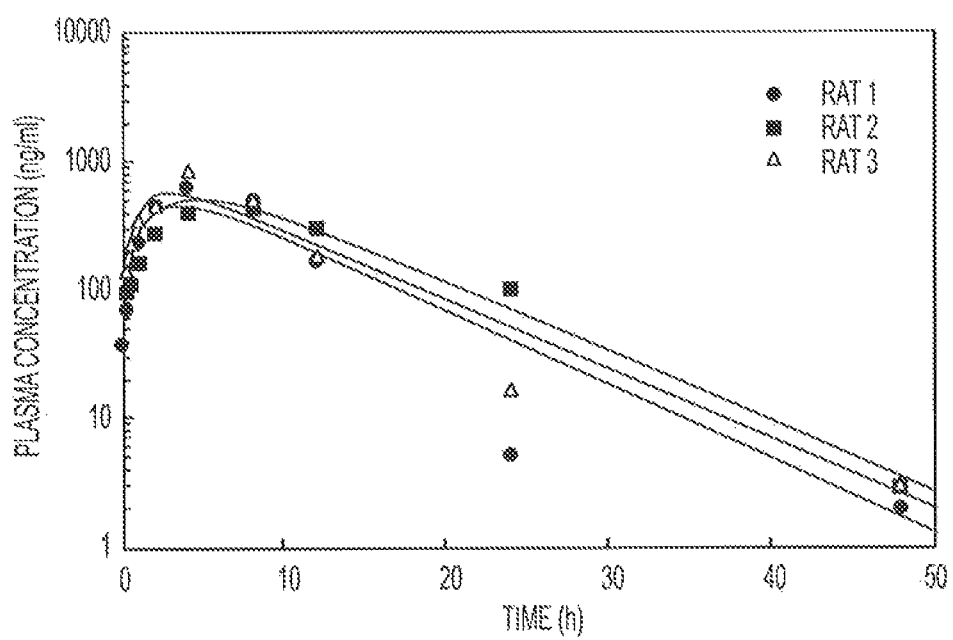
FIG. 4: Graphically depicts plasma concentration-time profile of topotecan after subcutaneous administration of the hydrogel containing TPT solution (10 mg/kg) to Fischer 344 rats. Hydrogels containing TPT solution (5 mg/ml) were prepared from 4% (w/v) copolymer and the crosslinker PEGDVS in phosphate buffer pH 7.0.

The plasma profile following s.c. administration of TPT entrapped in the hydrogel was modeled using a one-compartment model with first-order absorption and elimination (FIG. 4). The absorption half life $t_{1/2}$ ($k_a$) of TPT trapped in the hydrogel injected s.c. was 5-fold greater than that of TPT solution administered s.c. since drug release into the subcutaneous tissue is dependent on the swelling of the hydrogel and diffusion of drug through the tortuous pathways within the hydrogel. This is reflected by the 2-fold increase in the tmax. The peak plasma concentrations ($C_{max}$) after subcutaneous injection of TPT solution and TPT in the hydrogel were similar (427.8±140.2 vs 537.3±33.5 ng/ml) but lower that that following the i.v. dosing of a TPT solution. The plasma profile for TPT administered subcutaneously as a solution was compared to that for TPT trapped in a hydrogel (FIG. 1). The similarity in these two profiles confirms the in vitro results that encapsulating free TPT in the hydrogel does not result in controlled release since the molecular weight of the drug is substantially smaller than that of the pore size in the hydrogel. Therefore upon swelling of the hydrogel, which is the rate limiting step, TPT is rapidly released from the hydrogel into the s.c. tissue and distributed into the systemic circulation.

d. Subcutaneous (s.c.) Administration of TPT Liposomes

Figure 5:
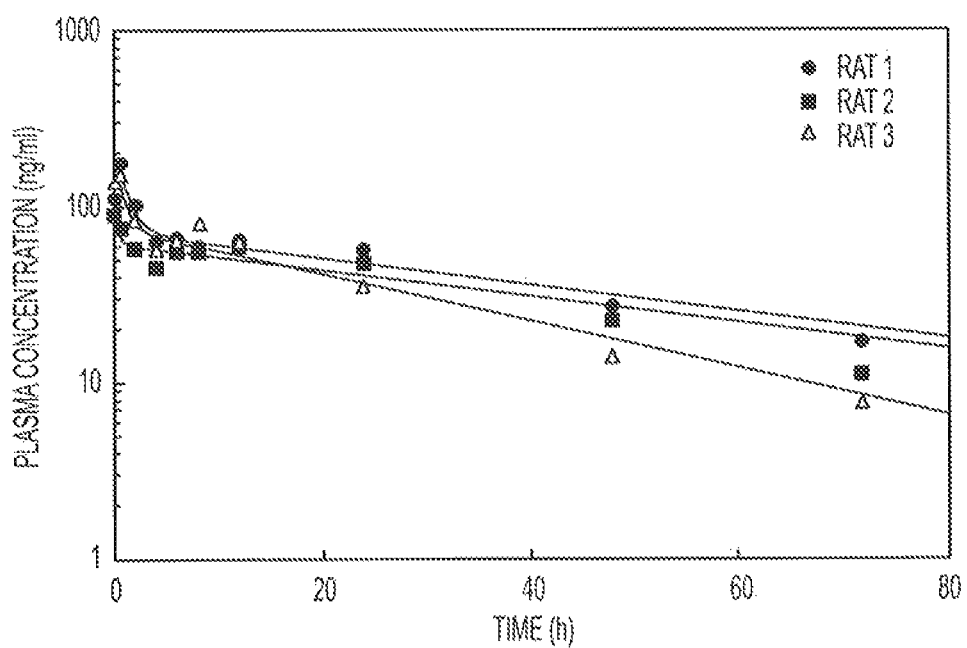
FIG. 5: Graphically depicts plasma concentration-time profile of topotecan after subcutaneous administration of TPT liposomes (10 mg/kg) to Fischer 344 rats. TPT loaded liposomes (5 mg/ml) were prepared in phosphate buffer pH 7.0.

The pharmacokinetics of TPT were greatly altered by entrapping TPT in liposomes. The pharmacokinetic data for the liposome formulation appeared to be consistent with a two compartment model with first-order absorption and elimination (Equation 5.3) (FIG. 5).

$$C_p = Ae^{-\alpha^* t} + Be^{-\beta^* t} + Ce^{-k_{01}^* t} \qquad \text{Equation 5.3}$$

$C_p$=concentration of drug in plasma
A=y intercept for the distribution phase
B=y intercept for the elimination phase
C=y intercept for the absorption phase
α=distribution rate constant
β=elimination rate constant
$k_{01}$=absorption rate constant
t=time The appearance of TPT from the s.c. site into the central compartment following the s.c. administration liposomes was rapid compared to that of TPT solution (absorption half, t½(ka)=0.068±0.02 vs 0.32±0.05 h, respectively). However, the plasma elimination rate was relatively slow with the liposomal formulation (elimination phase half-life, $t_{1/2}$=35.06±6.10 vs 6.42±1.99 h) suggesting that it is confounded to some extent by the rate at which the drug presents to the central compartment. The appearance of TPT in the systemic circulation after the administration of TPT liposomes is complex as it involves a combination of two rate constants; the release rate of drug from the liposomes and the rate of appearance of the released drug in the central compartment. Since the appearance of drug in the systemic circulation was much faster for the liposome formulation compared with the TPT solution, the release rate of TPT from the liposomes was not the rate determining step for drug distribution from the s.c. site ($k_a$=13.22 h$^{-1}$ vs 2.31 h$^{-1}$). Liposomes are known to enhance intracellular drug concentration by fusing with the cell membrane and depositing the drug directly into the cell. Therefore, this could explain the rapid appearance of TPT in the systemic circulation after the s.c. administration of TPT liposomes.

Figure 6:
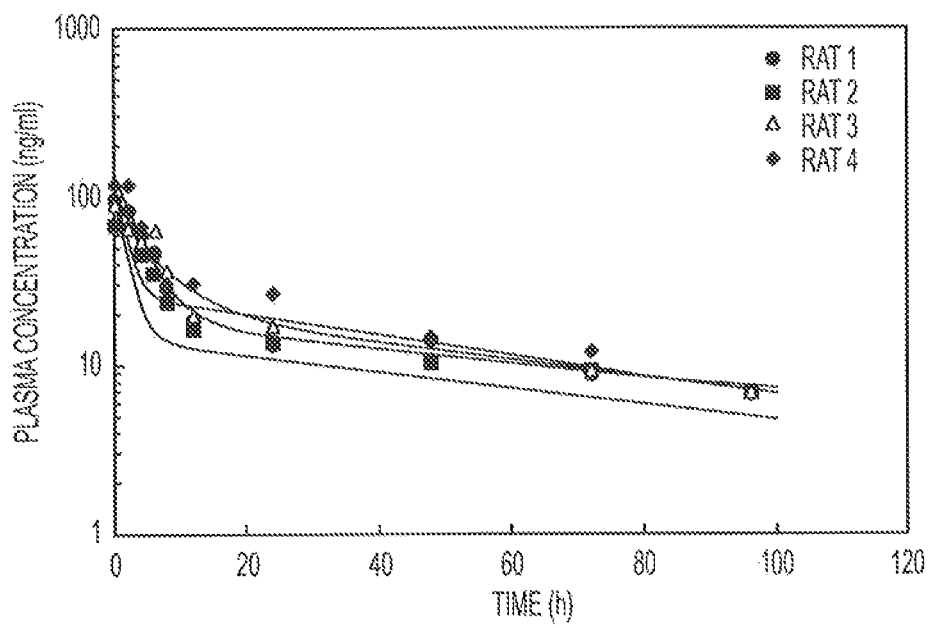
FIG. 6: Graphically depicts plasma concentration-time profile of topotecan after subcutaneous administration of TPT loaded liposomes entrapped in the hydrogel (10 mg/kg) to Fischer 344 rats. Hydrogels containing TPT liposomes (5 mg/ml) were prepared from 4% (w/v) copolymer and the crosslinker PEGDVS.

After the s.c. injection of TPT liposomes the drug-plasma profile exhibited a small burst followed by a gradual decline in the plasma level of TPT over several hours. The burst effect is probably due to the release of drug present on the surface of the liposomes. The slow elimination rate constant results in a significantly longer half-life and a gradual decrease in the drug-plasma levels. The AUC for TPT liposomes was less than half that resulting from the TPT solution (3560.46±509.67 vs 5798.26±893.99 h·ng·ml$^{-1}$). Therefore, the body was exposed to less drug despite the administration of similar doses. This was possibly due to the lower bioavailability of this delivery system (F=0.766 vs 0.988) (FIG. 5).

e. Subcutaneous (s.c.) Administration of TPT Liposomes Entrapped in the Hydrogel The entrapment of TPT liposomes in the hydrogel resulted in first-order drug release from the s.c. site into the systemic circulation. The plasma-concentration profile declined biphasically and was fitted to a two compartment model (FIG. 6). With the TPT liposomes in the hydrogel, the systemic appearance of drug after s.c. injection, in terms of dose fraction (F), was 49%. The $C_{max}$ following s.c. injection of TPT liposomes in the hydrogel was 4-fold lower than that after s.c. administration of a TPT solution (106.86±13.03 vs 431.65±137.92 ng/ml). The $C_{max}$ for the TPT liposomes in the hydrogel was followed by a steady-state plasma concentration of 10 ng/mL over several hours as drug was slowly being released from the hydrogel into the s.c. site prior to the systemic circulation.

The rate of appearance of TPT in the central compartment following the s.c administration of TPT liposomes in the hydrogel was slower than that of free TPT liposomes since drug release was hindered by both the liposomal and hydrogel barriers ($k_a$=5.29 h$^{-1}$ vs 13.22 h$^{-1}$). The elimination half life was slower following the administration of TPT liposomes in the hydrogel compared to TPT solution (elimination phase half-life, t½(β)=89.25±15.62 vs 6.42±1.99 h) as the drug continued to appear in the central compartment while elimination was occurring. The plasma profiles following the administration of TPT liposomes and TPT liposomes entrapped in the hydrogel were similar, except that the terminal slope for the liposomes in the hydrogel was nearly horizontal after 24 hours (elimination phase half-life, t½(β)=89.25±15.62 vs 35.06±6.10 h), representing a controlled release system.

The TPT liposomes were ~100 nm in size which is similar to that of the pore size in the hydrogel. The liposomes, therefore, were well trapped within the hydrogel and drug release from this system was a combination of two mechanisms. These mechanisms include the diffusion of either intact liposomes along the tortuous pathways in the hydrogel formed as the gel absorbs water and swells, or the release of free drug from the trapped liposomes which diffuses through the hydrogel into the s.c tissue. Therefore, encapsulating drug-loaded liposomes within the hydrogel provides a second barrier to drug release, resulting in the controlled release of small molecular weight hydrophilic drugs.

Determination of the Absorption Rate

The Wagner-Nelson method is used to determine the absorption rate (ka) of a drug. This method assumes that the amount of drug absorbed into the systemic circulation at any time after the administration equals the sum of the amount of drug remaining in the body plus the cumulative amount of drug that has already been eliminated. The fraction of drug absorbed at any time is:

$$\frac{Ab}{Ab^\infty} = \frac{C_p + k_{el}[AUC]_0^t}{k_{el}[AUC]_0^\infty} \quad \text{Equation 5.4}$$

Figure 7:
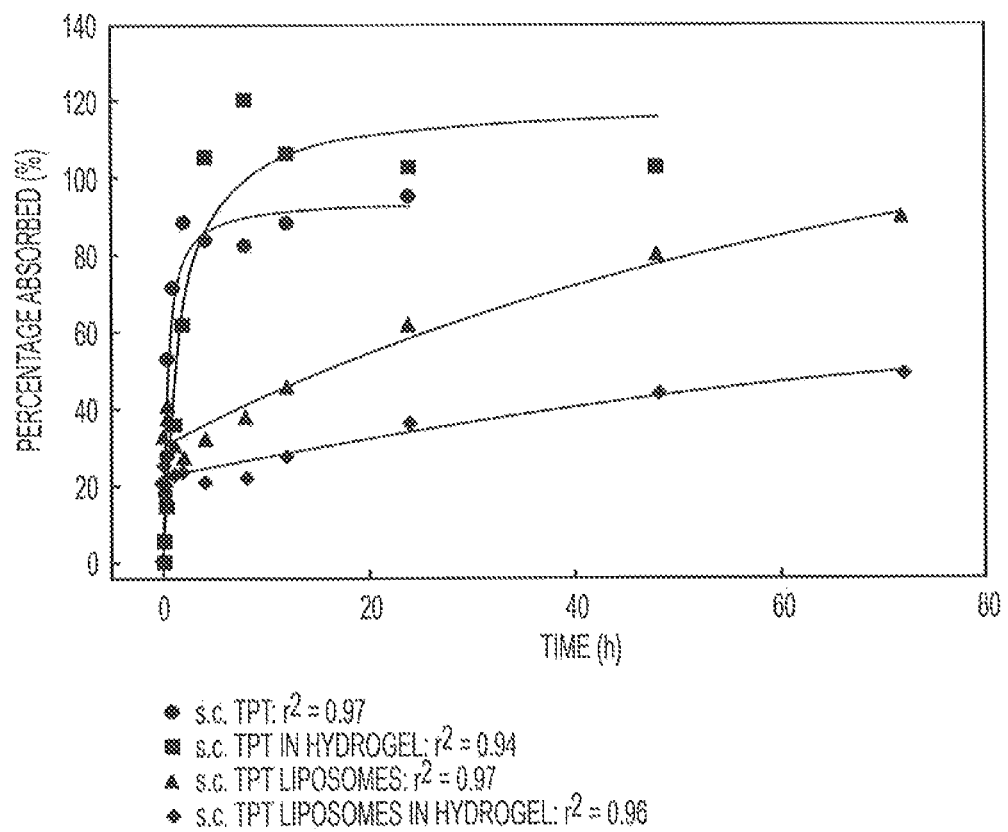
FIG. 7: Graphically depicts Wagner-Nelson Plot of the percent of TPT absorbed after the administration of various formulations of TPT.

Ab=amount of drug absorbed at t=∞
Ab=amount of drug absorbed
$C_p$=concentration of drug in plasma The systemic absorption profiles of TPT following subcutaneous injection are calculated using Equation 5.4 and shown in FIG. 7. Free TPT liposomes and TPT liposomes entrapped in the hydrogel showed an initial rapid release followed by a more gradual rate of release. This profile is desirable for controlled-release systems where the initial release rate should be sufficiently rapid to ensure that therapeutic blood levels are achieved in a timely manner while toxic levels are avoided. Absorption of TPT from a s.c. TPT solution was nearly complete (>85%) in 2 h while that from TPT liposomes and TPT liposomes in the hydrogel were similar, with only ~25% absorbed after 2 h. At 72 h 89% of TPT was released from the liposomes while only 48% was released from the liposomes in the hydrogel. Therefore, entrapping the liposomes in the hydrogel further controlled the release of TPT because the hydrogel provided an additional barrier to drug release.

Figure 8:
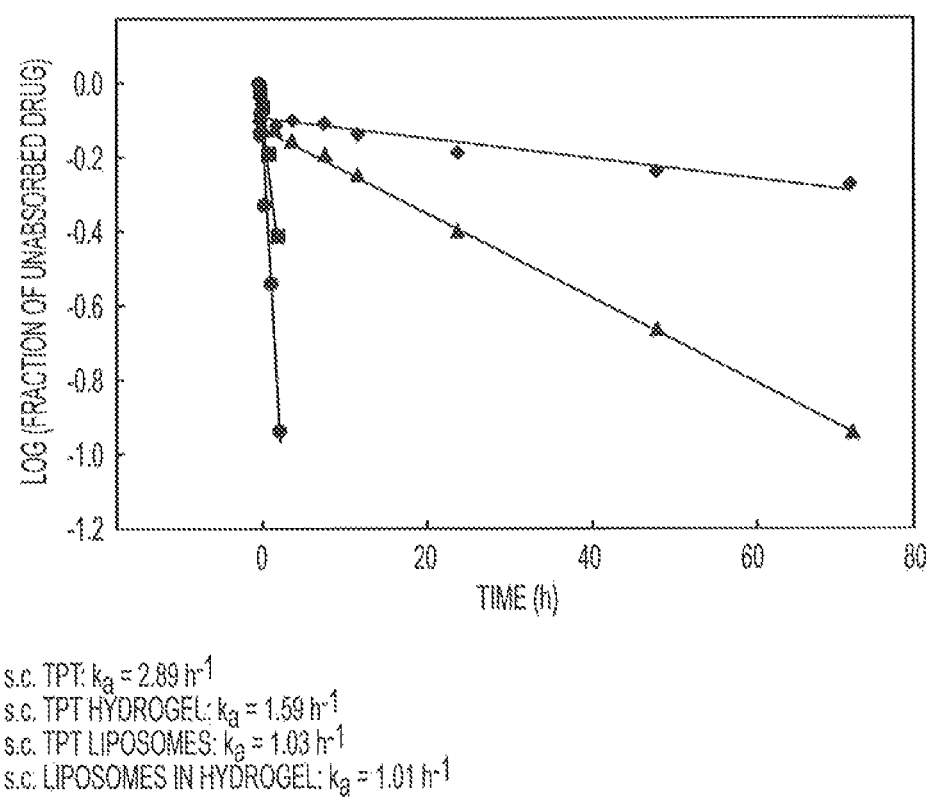
FIG. 8: Graphically depict determination of the ka values for the various TPT formulations. The Wagner-Nelson equation was used in the calculation of the ka values based on the assumption that the elimination rate was fixed to that determined after i.v. administration of TPT.

From the slope of the plot of the fraction unabsorbed $(1-(Ab/Ab^\infty))$ versus time, the $k_a$ values for each delivery system can be determined (FIG. 8). Using this method the kel is fixed to that obtained after i.v. administration of TPT and thus the true ka value can be determined. The ka value decreased when TPT was entrapped in the hydrogel as the drug has to be released from the hydrogel into the s.c. site prior to entering the systemic circulation. The TPT liposomes and liposomes entrapped in the hydrogel have similar absorption rates, which are approximately half that of the free TPT. In both these delivery systems the absorption rate is governed by the release rate. Therefore, encapsulating TPT in liposomes which are entrapped in the hydrogel results in the prolonged release of drug and subsequently constant TPT plasma levels.

Encapsulating drugs in liposomes can alter their pharmacokinetics and biodistribution resulting in improved efficacy and reduced toxicity. For the CPTs, an additional benefit is the protection of the active lactone species.

Example 6

Pharmacodynamic Study

Tumor growth delay or tumor control are two appropriate end points used in analyzing solid tumors. If treatment is initiated prior to tumor development the experiment is designated a tumor-growth inhibition study. However, if treatment begins once an established tumor nodule is present the experiment is designated a tumor-growth delay study. Tumor-growth delay studies are preferable as they are a better model of clinical disease.

Tumor Weights are Estimated from Two-Dimensional Measurements:

$$\text{Tumor Weight} = \frac{a(b)^2}{2} \quad \text{Equation 4.5}$$

Where $a$ and $b$ are the tumor length and width respectively

A. Cells and Cell Culture

Mat B-III cells were obtained from American Type Culture Collection (Rockville, Md.). The cells were maintained in culture in vitro in RMPI medium supplemented with 10% fetal bovine serum, 100 units/ml penicillin-streptomycin sulfate, 2% sodium bicarbonate and 1% non-essential amino acids.

B. Tumor Induction

Female Fischer 344 rats (160-180 g) were purchased from Hilltop Laboratories (Scottdale, Pa.) and allowed to acclimate for one week. The rats were housed, two per cage and tagged to facilitate identification. Mat B-III cells grown in serum-containing medium were washed with phosphate buffer and trypsinized for 5 minutes. The cells were collected and centrifuged for 5 minutes. The cell pellet was resuspended in Dulbecco's phosphate buffer (DPBS) and centrifuged as above. This process was repeated three times. Finally the cell pellet ($2\times10^6$ cells/ml) was resuspended and the cells were injected (0.5 ml=$1\times10^6$ cells) subcutaneously into the back of the rats. The rats were weighed daily and examined for tumor development and distress. The tumor size was measured in two dimensions using calipers and the tumor mass was calculated as described in Equation 4.5.

C. Drug Treatment

Once the tumors reached a size of approximately 1 $cm^3$, (500-1000 mg) the rats were randomized into five experimental groups. The rats received either 0.2 mL normal saline, 0.2 mL of blank liposomes loaded in a 4% (w/v) blank hydrogel, 0.2 mL of TPT (5 mg/mL in normal saline pH 2.56, Dose: 5 mg/kg), 0.2 mL of TPT liposomes (5 mg/mL, Dose: 5 mg/kg) or 0.2 mL of TPT liposomes trapped in the hydrogel (Dose: 5 mg/kg). All treatments were administered s.c. in the vicinity of the tumor. The rats were monitored daily for weight loss, tumor growth, skin lesions, distress or ascites. Body weight loss and lethal toxicity were taken into account when evaluating the toxic effects induced by the drug treatment. The experiment was terminated at day 16 after administration of the treatment or once the tumor mass reached 10% of the animal's body weight or the animal body weight decreased by more than 20% of the starting weight. The tumors were surgically removed and the final weight noted.

Although the Mat B-III cells are syngeneic to the immunocompetent Fischer 344 rats, tumors developed at different rates perhaps depending on variations in each animal's immune response or other biological parameters. Therefore, to adequately compare the various treatments, the rats were divided into two groups of 16 rats each based on the size of the tumors on day 10 following inoculation (small tumor group: size ~500 mg and large tumor group: size ~1000 mg). Within each group, the rats were further divided to receive one of the following five treatments: normal saline, blank liposomes loaded in a blank 4% (w/v) hydrogel, TPT solution, TPT liposomes or TPT liposomes loaded in a 4% (w/v) hydrogel. The dimensions of the tumors were measured prior to and post administration of the treatments in the case of the hydrogel groups to account for the volume of hydrogel.

Due to the high plasma levels achieved after the administration of TPT solution, as confirmed with the pharmacokinetic analysis, all rats in this treatment group lost weight. TPT is known to cause diarrhoea and decrease appetite. The group that received TPT liposomes loaded in the hydrogel exhibited minimal weight loss, as this formulation did not result in high plasma concentrations. The rats all regained weight with time and no animals died, confirming that the dose administered was not lethally toxic.

Figure 9A:
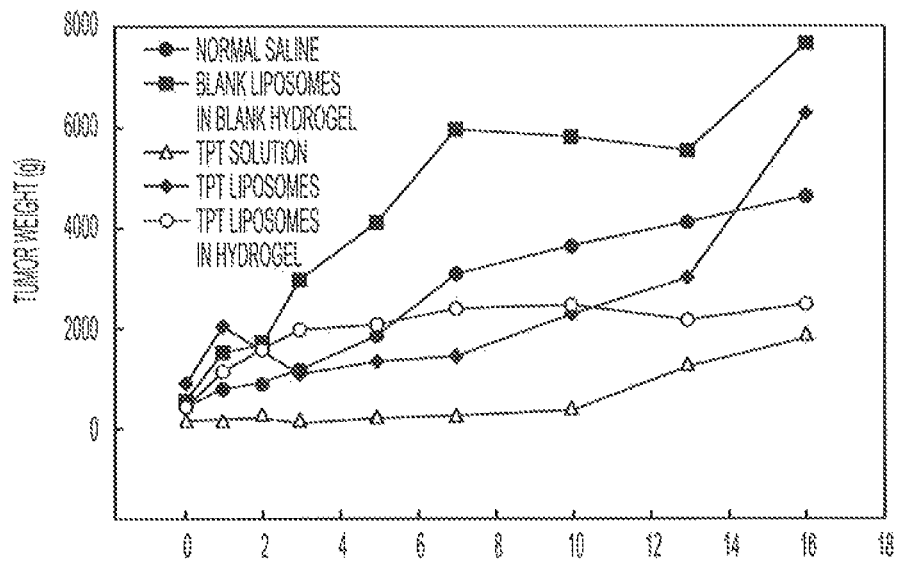
FIGS. 9 A and B: Graphically depict growth curves (A) and percent change in tumor weight (B) of small (starting weight<500 g) Mat-B III tumors treated with various formulations. Results represent mean of 3 tumors per group.
Figure 9B:
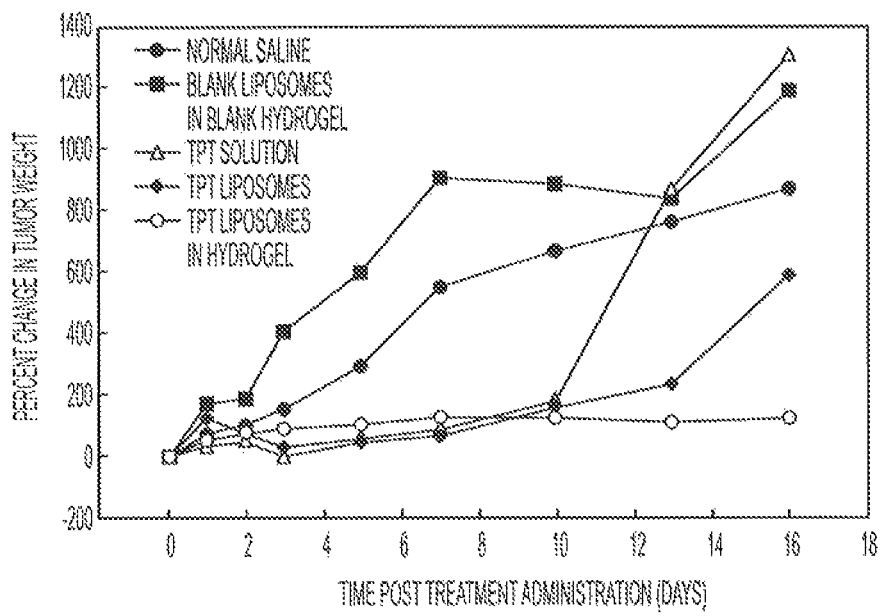

The tumor size was monitored every second day and the weight calculated based on Equation 4.5. Administration of the hydrogel (200 μL) in the vicinity of the tumor resulted in a doubling of the tumor size. Subsequent tumor volumes were corrected for by taking the initial change in tumor size into consideration. However, since the hydrogel also swells in the presence of fluid, this increase in size could not be taken into consideration. In the small tumor group, TPT solution and TPT liposomes were very effective initially in reducing tumor size (FIG. 9). However, 7 to 10 days after the initiation of treatment the tumors began to regrow as the drug was completely cleared from the circulation and the remaining tumor cells began to multiply. Tumor size in the group treated with TPT liposomes loaded in the hydrogel increased initially followed by growth stabilization. The initial increase could be attributed to the swelling of the hydrogel. This treatment group was the most efficacious over the 16 day period, possibly because the drug containing hydrogel surrounded the tumor and slowly released drug into the tumor.

Figure 10A:
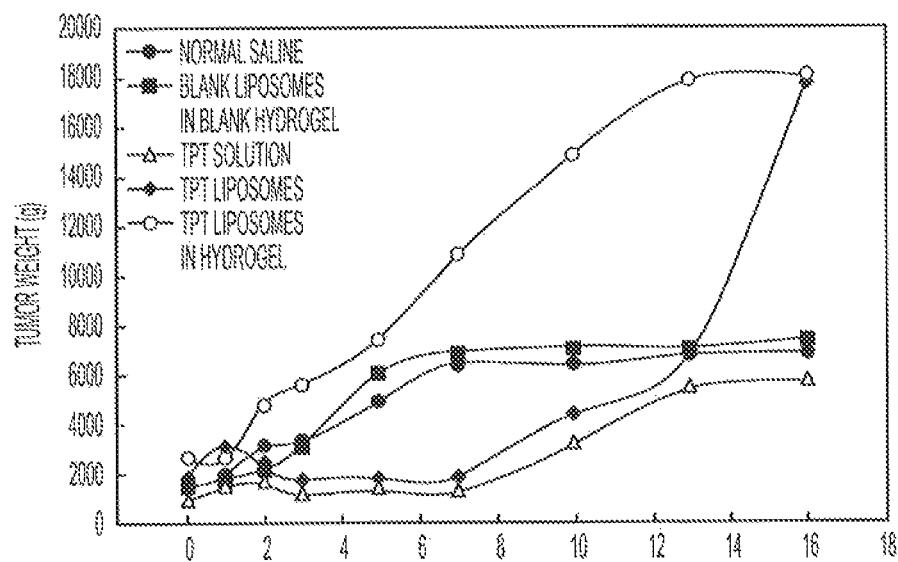
FIGS. 10 A and B: Graphically depict growth curves (A) and percent change in tumor weight (B) of large (starting weight~1000 g) Mat B-III tumors treated with various formulations. Results represent mean of 3 tumors per group.
Figure 10B:
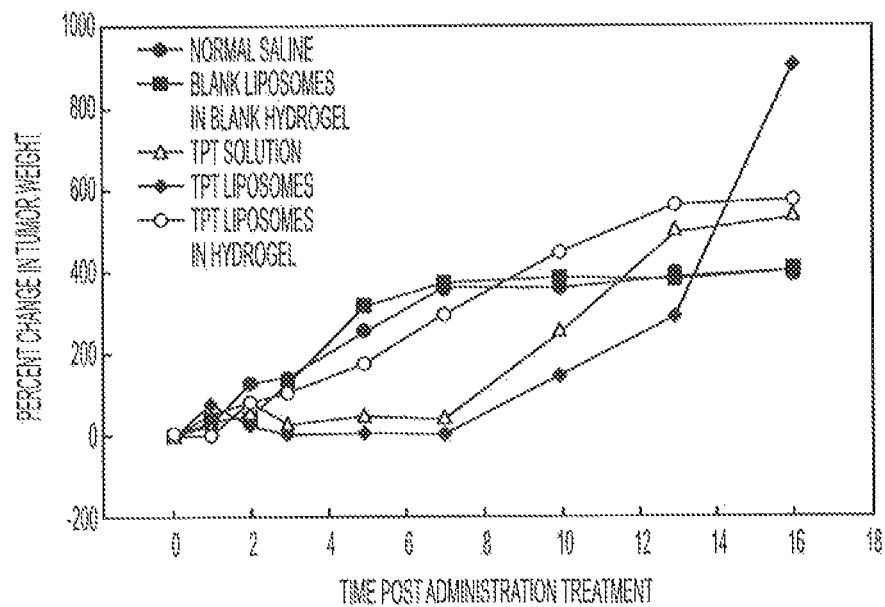

Similarly, in the large tumor group, TPT solution and TPT liposomes were initially effective, but tumor growth reoccurred once the drug was cleared from the circulation (FIG. 10). TPT liposomes loaded in the hydrogel were not effective in reducing tumor size in this group possibly because drug release was too slow. Therefore, the concentration of drug at the tumor site was inadequate to cause suppression of tumor growth in large, well-developed tumors. Therefore, this controlled release formulation is most suitable for the treatment of small tumors or in situations where tumors have been partially surgically resected.

Upon completion of the study or once the tumors reached the maximum size, the rats were euthanized using carbon dioxide and the tumors were resected. The tumors in the rats that received either no treatment, TPT solution or TPT liposomes were highly vascularized and firm. In the rats that received the hydrogel treatment, the tumors were less dense and not well vascularized. The administration of the hydrogel did not elicit an immune response as there was no fibrous capsule around the tumor.

Many other variations of the present invention will be apparent to those skilled in the art and are meant to be within the scope of the claims appended hereto.

What is claimed is:

1. A method of administering a chemotherapeutic agent to a patient diagnosed with cancer over a prolonged period of time, said method comprising subcutaneously administering to said patient a controlled release resorbable hydrogel composition consisting essentially of: (a) a cross-linked polymer matrix consisting of poly(ethylene glycols) containing thiol groups that are cross-linked with a thiol reactive bi-functional cross-linking reagent wherein said reagent reacts with two thiols, and (b) a plurality of liposomes, encapsulating the chemotherapeutic agent, and physically entrapped within said cross-linked polymer matrix;

wherein said chemotherapeutic agent is selected from the group consisting of camptothecin, analogs thereof and pharmaceutically acceptable salts thereof, and said entrapment of said liposomes within said cross-linked polymer matrix of said hydrogel provides a decrease in the $C_{max}$ of said chemotherapeutic agent when said composition is administered subcutaneously, as compared to equivalent doses of the same chemotherapeutic agent administered subcutaneously in an equivalent non-cross-linked hydrogel formulation.

2. The method of claim 1, wherein said hydrogel composition releases the chemotherapeutic agent over a period of at least about 24 hours.

3. The method of claim 1, wherein the cancer is selected from the group consisting of leukemia, colon cancer, lung cancer, prostate cancer, ovarian cancer, and breast cancer.

4. The method of claim 1, wherein said polymer matrix is prepared from a ω-diamino-poly (ethylene glycol) and thiomalic acid; a co-dihydroxy-poly (ethylene glycol) and thiomalic acid; or a ω-dicarboxy-PEG-subunits and lysine, wherein free carboxy groups on said lysine are derivatized to provide thiol groups.

5. The method of claim 4, wherein said thiol groups on said polymer are cross-linked by thioether or disulfide bonds.

6. The method of claim 1, wherein said matrix has at least one controlled release in-vivo kinetic profile selected from the group consisting of zero order, pseudo zero order, and first order.

7. The method of claim 1, wherein said matrix provides a constant rate of release of chemotherapeutic agent.

8. The method of claim 1, wherein said cross-linked polymer is a diamino polyethyleneglycol crosslinked with a cross-linking agent selected from the group consisting of a bifunctional disulfide-forming cross-linking agent, a bifunctional thioether-forming cross-linking agent, and combinations thereof.

9. The method of claim 1, wherein the composition is subcutaneously administered in proximity to a cancer tumor.

10. The method of claim 1, wherein said chemotherapeutic agent diffuses at a controlled rate from said hydrogel composition in situ.

11. The method of claim 1, wherein said chemotherapeutic agent is loaded into said liposomes through an active loading process.

12. The method of claim 1, wherein said liposomes comprise a wall material selected from the group consisting of a phosphatidic acid, a phosphatidyl choline with both saturated and unsaturated lipids, a phosphatidyl ethanolamine, a phosphatidylglycerol, a phosphatidylserines, a phosphatidylinositols, a lysophosphatidyl derivatives, a cardiolipin, γ-alkyl phospholipids, and combinations thereof.

13. The method of claim 1, wherein said chemotherapeutic agent is selected from the group consisting of topotecan, irinotecan, homocaptothecins, homosilatecans and pharmaceutically acceptable salts thereof.

14. The method of claim 1, wherein said cancer is selected from the group consisting of cancers of the esophagus, the stomach, the intestines, the rectum, the oral cavity, the pharynx, the larynx, the lung, the colon, the breast, the cervix uteri, the corpus endometrium, the ovaries, the prostate, the testicles, the bladder, the kidneys, the liver, the pancreas, the bone, the connective tissues, the skin, the eyes, the brain and the central nervous system, cancer of the thyroid, leukemia, Hodgkin's disease, lymphomas other than those related to Hodgkin's, multiple myelomas and combinations thereof.

15. The method of claim 1, wherein the chemotherapeutic agent is 9-amino-dimethyl-10-hydroxycamptothecin (TPT).

* * * * *